United States Patent [19]

Sakane et al.

[11] Patent Number: 5,173,485

[45] Date of Patent: Dec. 22, 1992

[54] CEPHEM COMPOUNDS

[75] Inventors: Kazuo Sakane, Kawanishi; Kohji Kawabata, Osaka; Yoshiko Inamoto, Toyonaka, all of Japan

[73] Assignee: Fujisawa Pharmaceutical Company, Ltd., Osaka, Japan

[21] Appl. No.: 714,995

[22] Filed: Jun. 14, 1991

Related U.S. Application Data

[63] Continuation of Ser. No. 317,981, Mar. 2, 1989, abandoned.

[30] Foreign Application Priority Data

Mar. 9, 1988 [GB] United Kingdom ............... 8805642

[51] Int. Cl.$^5$ ............... C07D 501/46; A61K 31/545
[52] U.S. Cl. ................................ 514/202; 540/222; 540/225
[58] Field of Search ............... 540/222; 514/202

[56] References Cited

U.S. PATENT DOCUMENTS

| | | | |
|---|---|---|---|
| 4,665,065 | 5/1987 | Miyake et al. ........... | 514/202 |
| 4,921,851 | 5/1990 | Kishimoto et al. ........ | 540/222 |
| 4,962,100 | 10/1990 | Miyake et al. ........... | 540/222 |

FOREIGN PATENT DOCUMENTS

| | | |
|---|---|---|
| 0304858 | 8/1987 | European Pat. Off. |
| 61-286389 | 12/1986 | Japan. |

OTHER PUBLICATIONS

Chemical Abstracts vol. 112(23):216538k (1990).

Primary Examiner—Nicholas S. Rizzo
Attorney, Agent, or Firm—Oblon, Spivak, McClelland, Maier & Neustadt

[57] ABSTRACT

The invention relates to an antimicrobial compound of the formula:

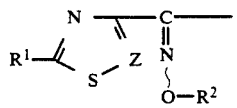

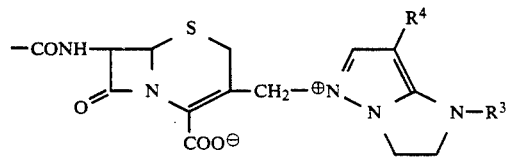

wherein
$R^1$ is amino or a protected amino group,
$R^2$ is lower alkyl, lower alkenyl, carboxy (lower) alkyl or protected carboxy(lower)alkyl,
$R^3$ is hydrogen, lower alkyl, hydroxy(lower)alkyl, protected hydroxy(lower)alkyl, amino(lower)alkyl, protected amino(lower)alkyl or lower alkanoyl,
$R^4$ is hydrogen, lower alkyl or lower alkylthio, and
Z is N or CH or a pharmaceutically acceptable salt thereof.

12 Claims, No Drawings

CEPHEM COMPOUNDS

This application is a continuation of application Ser. No. 07/317,981, filed on Mar. 2, 1989, now abandoned.

The present invention relates to new cephem compounds and pharmaceutically acceptable salts thereof.

More particularly, it relates to new cephem compounds and pharmaceutically acceptable salts thereof, which have antimicrobial activities, to processes for preparation thereof, to pharmaceutical composition comprising the same, and to a method for treating infectious diseases in human being and animals.

Accordingly, one object of the present invention is to provide the cephem compounds and pharmaceutically acceptable salts thereof, which are highly active against a number of pathogenic microorganisms.

Another object of the present invention is to provide processes for the preparation of the cephem compounds and salts thereof.

A further object of the present invention is to provide pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula (I):

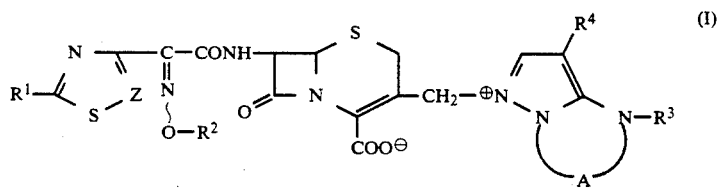

wherein
$R^1$ is amino or a protected amino group,
$R^2$ is an organic group,
$R^3$ is hydrogen, lower alkyl, hydroxy(lower)alkyl, protected hydroxy(lower)alkyl, amino(lower)alkyl, protected amino(lower)alkyl or an imino protective group,
$R^4$ is hydrogen, lower alkyl or lower alkylthio,
A is lower alkylene which may be substituted with suitable substituent(s), and
Z is N or CH.

The cephem compound (I) of the present invention can be prepared by processes as illustrated in the following.

Process 1

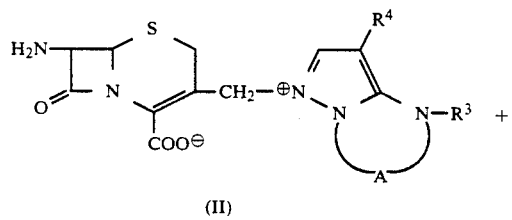

(II)
or its reactive derivative
at the amino group
or a salt thereof

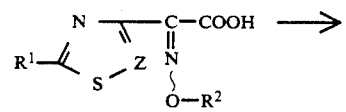

(III)
or its reactive derivative
at the carboxy group
or a salt thereof

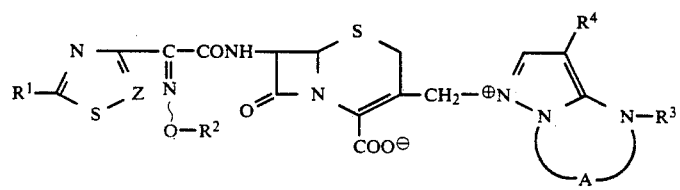

(I)
or a salt thereof

-continued
Process 2
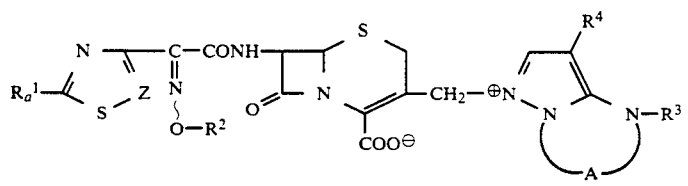
(Ia)
or a salt thereof
↓ Elimination reaction of the amino protective group
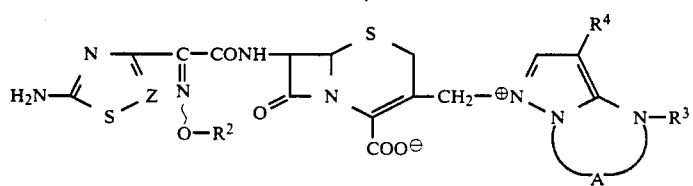
(Ib)
or a salt thereof
Process 3
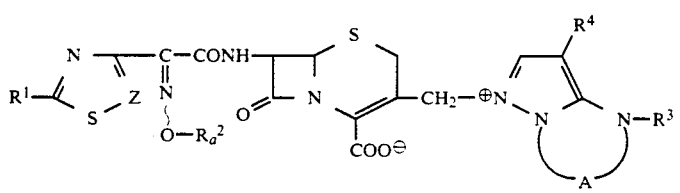
(Ic)
or a salt thereof
↓ Elimination reaction of the carboxy protective group
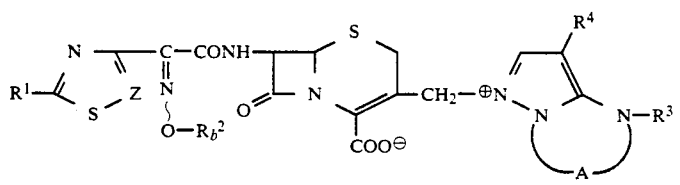
(Id)
or a salt thereof
Process 4
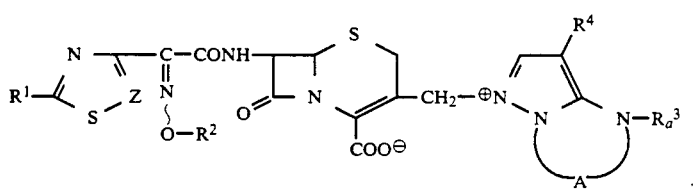
(Ie)
or a salt thereof
↓ Elimination reaction of the amino protective group

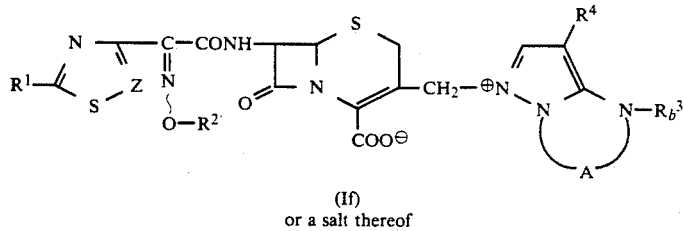

(If)
or a salt thereof wherein
R¹, R², R³, R⁴, A and Z are each as defined above,
$R_a^1$ is a protected amino group,
$R_a^2$ is protected carboxy(lower)alkyl,
$R_b^2$ is carboxy(lower)alkyl,
$R_a^3$ is protected amino(lower)alkyl and
$R_b^3$ is amino(lower)alkyl.

The starting compound (II) is novel and can be prepared by processes as illustrated in the following.

Process A

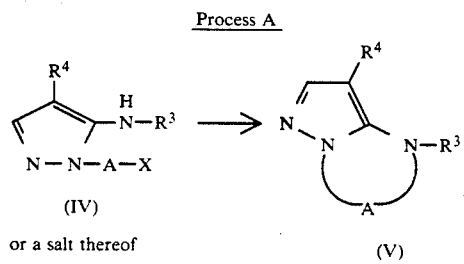

(IV)
or a salt thereof (V)
or a salt thereof

Process B

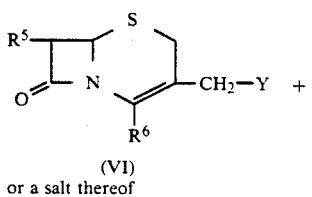

(VI)
or a salt thereof

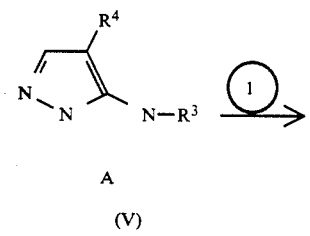

(V)
or a salt thereof

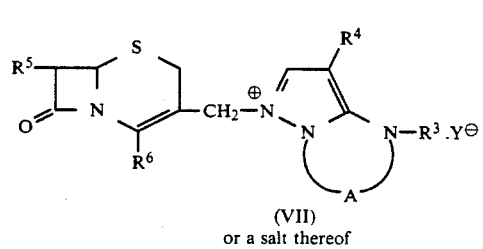

(VII)
or a salt thereof

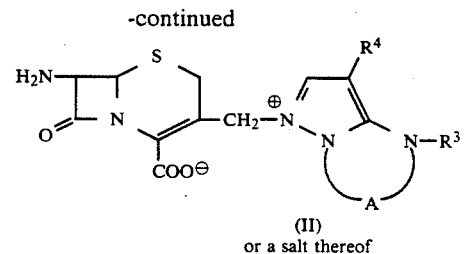

(II)
or a salt thereof

Process C

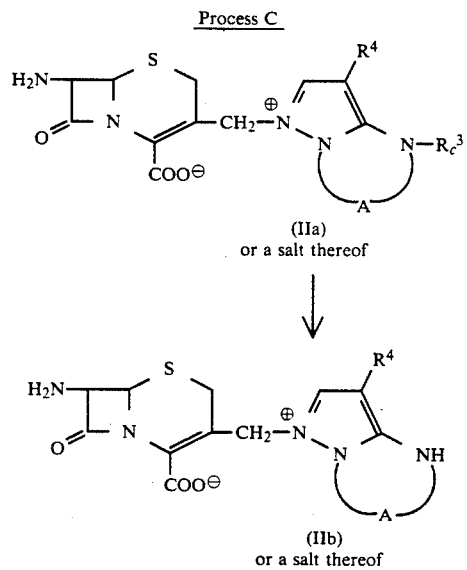

(IIa)
or a salt thereof (IIb)
or a salt thereof wherein
R³, R⁴ and A are each as defined above,
X is an acid residue,
R⁵ is a protected amino group,
R⁶ is a protected carboxy group,
Y is an acid residue, and
$R_c^3$ is an imino protective group.

Further, the compound (V) or a salt thereof can be prepared also by the methods disclosed in the Preparations described later or similar manners thereto.

Regarding the compounds (I), (Ia), (Ib), (Ic), (Id), (Ie), (If) and (III), it is to be understood that said compounds include syn isomer, anti isomer and a mixture thereof. For example, with regard to the object compound (I), syn isomer means one geometrical isomer having the partial structure represented by the following formula:

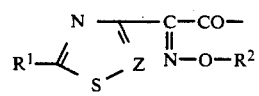

(wherein R¹, R² and Z are each as defined above) and anti isomer means the other geometrical isomer having the partial structure represented by the following formula:

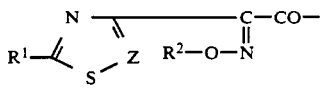

(wherein R¹, R² and Z are each as defined above).

Regarding the other compounds, as mentioned above, the syn isomer and the anti isomer can also be referred to the same geometrical isomers as illustrated for the compound (I).

Suitable pharmaceutically acceptable salts of the object compound (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s) unless otherwise indicated.

Suitable "protected amino" and "protected amino moiety" in the term "protected amino(lower)alkyl" may include an acylamino or an amino group substituted by a conventional protective group such as ar(-lower)alkyl which may have suitable substituent(s) (e.g. benzyl, trityl, etc.) or the like.

Suitable "acyl moiety" in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like. The acyl moiety as stated above may have suitable substituent(s) such as halogen (e.g. chlorine, bromine, iodine or fluorine) or the like.

Suitable "organic group" may include lower alkyl, mono(or di or tri)halo(lower)alkyl (e.g. chloromethyl, dichloromethyl, trichloromethyl, bromomethyl, chloroethyl, dichloroethyl, trichloroethyl, fluoroethyl, trifluoroethyl, etc.), lower alkenyl (e.g., vinyl, 1-propenyl, allyl, 1-methylallyl, 1 or 2 or 3 butenyl, 1 or 2 or 3 or 4-pentenyl, 1 or 2 or 3 or 4 or 5-hexenyl, etc.), lower alkynyl (e.g., ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl, etc.), aryl (e.g., phenyl, naphthyl, etc.), ar(lower)alkyl such as phenyl(lower)alkyl (e.g., benzyl, phenethyl, phenylpropyl, etc.), carboxy(lower)alkyl, protected carboxy(lower)alkyl, and the like.

Suitable "protected carboxy" and "protected carboxy moiety" in the term "protected carboxy(lower)alkyl" may include esterified carboxy and the like. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.); lower alkenyl ester (e.g., vinyl ester, allyl ester, etc.); lower alkynyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)-halo(lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g., mesylmethyl ester, 2-mesylethyl ester etc.); ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g. phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "lower alkyl" and "lower alkyl moiety" in the terms "hydroxy(lower)alkyl", "protected hydroxy(lower)alkyl", "lower alkylthio", "carboxy(lower)alkyl", "protected carboxy(lower)alkyl", "amino(lower)alkyl" and "protected amino(lower)alkyl" may include straight or branched one such as methyl, ethyl, propyl, isopropyl, butyl, isobutyl, tert-butyl, pentyl, hexyl or the like.

Suitable "hydroxy protective group" in the term "protected hydroxy(lower)alkyl" may include an acyl group as exemplified above, and the like.

Suitable "imino protective group" may include an acyl group as exemplified above, and the like.

Suitable "lower alkylene" may include methylene, ethylene, trimethylene, tetramethylene, pentamethylene, hexamethylene and the like.

Suitable "substituent" in the term "lower alkylene which may be substituted with suitable substituent(s)" may include oxo, hydroxy, protected hydroxy wherein hydroxy protective group can be referred to the ones as exemplified above, and the like.

Suitable "acid residue" may include halogen [e.g. chlorine, bromine, iodine, etc.], acyloxy such as sulfonyloxy [e.g. benzenesulfonyloxy, tosyloxy, mesyloxy, etc.], lower alkanoyloxy [e.g. acetyloxy, propionyloxy, etc.] or the like.

Preferred embodiments of the object compound (I) are as follows.

$R^1$ is amino or acylamino (more preferably lower alkanoylamino), $R^2$ is lower alkyl, lower alkenyl, carboxy(lower)alkyl or protected carboxy(lower)alkyl [more preferably esterified carboxy(lower)alkyl, most preferably lower alkoxycarbonyl(lower)alkyl], $R^3$ is hydrogen, lower alkyl, hydroxy(lower)alkyl, amino(lower)alkyl, protected amino(lower)alkyl [more preferably acylamino(lower)alkyl, most preferably lower alkanoylamino(lower)alkyl] or an imino protective group (more preferably an acyl group, most preferably lower alkanoyl), $R^4$ is hydrogen, lower alkyl or lower alkylthio, A is lower alkylene which may be substituted with an oxo or a hydroxy group [more preferably ($C_2$-$C_3$)alkylene which may be substituted with an oxo or a hydroxy group, most preferably ethylene, trimethylene, or trimethylene substituted with an oxo or a hydroxy group], and Z is N or CH.

The processes for preparing the object compounds of the present invention are explained in detail in the following.

Process 1

The compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The compound (Ib) or a salt thereof can be prepared by subjecting the compound (Ia) or a salt thereof to elimination reaction of the amino protective group. Suitable method of this elimination reaction may include conventional one such as hydrolysis, reduction and the like.

Suitable salts of the compounds (Ia) and (Ib) can be referred to the ones as exemplified for the compound (I).

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For Reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 3

The compound (Id) or a salt thereof can be prepared by subjecting the compound (Ic) or a salt thereof to elimination reaction of the carboxy protective group.

Suitable salts of the compounds (Ic) and (Id) can be referred to the ones as exemplified for the compound (I).

This reaction can be carried out in a similar manner to that of the aforementioned Process 2, and therefore the reagents to be used and the reaction conditions (e.g., solvent, reaction temperature, etc.) can be referred to those of the Process 2.

Process 4

The compound (If) or a salt thereof can be prepared by subjecting the compound (Ie) or a salt thereof to elimination reaction of the amino protective group.

Suitable salts of the compounds (Ie) and (If) can be referred to the ones as exemplified for the compound (I).

This reaction can be carried out in a similar manner to that of the aforementioned Process 2, and therefore the reagents to be used and the reaction conditions (e.g., solvent, reaction temperature, etc.) can be referred to those of the Process 2.

The processes for preparing the starting compounds are explained in the following.

Process A

The compound (V) or a salt thereof can be prepared by subjecting the compound (IV) or a salt thereof to cyclization reaction. This reaction can be referred to that of Preparation 1(3) as mentioned below.

Process B - ①

The compound (VII) or a salt thereof can be prepared by reacting the compound (VI) or a salt thereof with the compound (V) or a salt thereof.

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction. The reaction temperature is not critical, and the reaction is usually carried out at ambient temperature, under warming or under heating.

Process B - ②

The compound (II) or a salt thereof can be prepared by subjecting the compound (VII) or a salt thereof to elimination reaction of the amino protective group in $R^5$ and the carboxy protective group in $R^6$. This reaction can be carried out in a similar manner to that of the aforementioned Process 2, and therefore the reagents to be used and the reaction conditions (e.g., solvent, reaction temperature, etc.) can be referred to those of the Process 2.

Process C

The compound (IIb) or a salt thereof can be prepared by subjecting the compound (IIa) or a salt thereof to elimination reaction of the imino protective group. This reaction can be carried out in a similar manner to that of the aforementioned Process 2, and therefore the reagents to be used and the reaction conditions (e.g., solvent, reaction temperature, etc.) can be referred to those of the Process 2.

The present invention includes within the scope of the invention the case that protected hydroxy in "A" is transformed into hydroxy during this reaction.

The object compound (I) and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on MIC (minimal inhibitory concentration) of a representative compound of the compound (I) are shown in the following.

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of μg/ml after incubation at 37° C. for 20 hours.

Test Compound (1) 7β-[2-(2-Aminothiazol-4-yl)-2-methoxyiminoacetamido]-3-[2,3-dihydro-5-(1H-imidazo[1,2-b]pyrazolio)]methyl-3-cephem-4-carboxylate (syn isomer)

Test result:

| | MIC (μg/ml) |
|---|---|
| Test strain | Test Compound (1) |
| E. coli 31 | ≦0.025 |

For therapeutic administration, the object compound (I) and pharmaceutically acceptable salts thereof of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases, a kind of the compound (I) to be applied, etc., in general, amounts between 1 mg and about 4,000 mg or even more per day may be administered to a patient. An average single dose of about 50 mg, 100 mg, 250 mg, 500 mg, 1000 mg, of the object compound (I) of the present invention may be used in treating diseases infected by pathogenic microorganisms.

The following Preparations and Examples are given for the purpose of illustrating the present invention in more detail.

Preparation 1

(1) A mixture of acetic anhydride (44.5 ml) and formic acid (22.3 ml) was stirred at ambient temperature for an hour. To this mixture was added 1-(2-hydroxyethyl)-5-aminopyrazole (30 g) at 0°-10° C., and the mixture was stirred under ice-cooling for 30 minutes. The mixture was poured into ice-cold water, adjusted to pH 10.5 with 40% aqueous potassium carbonate, and stirred under ice-cooling for 30 minutes. The mixture was extracted with a mixture of tetrahydrofuran and ethyl acetate 6 times. The organic layer was dried over magnesium sulfate and evaporated in vacuo to give 1-(2-hydroxyethyl)-5-formamidopyrazole (30.8 g).

IR (Nujol): 3230, 1695, 1570, 1540 cm$^{-1}$.

NMR (DMSO-d$_6$, δ): 3.62-3.95 (2H, m), 3.98-4.32 (2H, m), 6.22 and 6.36 (1H, each d, J=3 Hz), 7.42 (1H, d, J=3 Hz), 8.32 and 8.36 (1H, each s).

(2) To a solution of 1-(2-hydroxyethyl)-5-formamidopyrazole (10 g) and triethylamine (18 ml) in methylene chloride (100 ml) was added dropwise methanesulfonyl chloride (8.5 ml) under ice-cooling. The mixture was stirred at 0° C. for 1.5 hours. The reaction mixture was poured into water (20 ml) and the methylene chloride layer was separated. The aqueous layer was reextracted with tetrahydrofuran twice. The organic layers were combined and dried over magnesium sulfate. The solvent was evaporated and the residue was subjected to column chromatography on silica gel (200 g) using ethyl acetate as an eluent. Fractions containing the object compound were combined and evaporated in vacuo to give 1-(2-methylsulfonyloxyethyl)-5-formamidopyrazole (3.2 g) as crystals.

mp: 101°-104° C.,

IR (Nujol): 3300, 1780, 1730, 1660-1680, 1540-1560 cm$^{-1}$.

NMR (DMSO-d$_6$, δ): 2.93 (3H, s), 4.18-4.60 (4H, m), 6.08-6.40 (1H, m), 7.33 (1H, d, J=2 Hz), 8.17-8.43 (1H, m), 9.97-10.63 (1H, m).

(3) To a solution of 1-(2-methylsulfonyloxyethyl)-5-formamidopyrazole (6.2 g) in N,N-dimethylformamide (60 ml) was added 62% sodium hydride (1.03 g) under ice-cooling. The mixture was stirred at the same condition for 3 hours. The reaction mixture was poured into ethyl acetate (300 ml) and the insoluble material was filtered off. The filtrate was evaporated under reduced pressure and the residue was subjected to column chromatography on silica gel (100 g) using a mixture of diisopropyl ether and ethyl acetate as an eluent. Fractions containing the object compound were combined and evaporated in vacuo to give 1-formyl-2,3-dihydro-1H-imidazo[1,2-b]pyrazole (3.91 g) as crystals.

mp: 78°-80° C.

IR (Nujol): 1650, 1570, 1520 cm$^{-1}$.

NMR (CDCl$_3$, δ): 4.10-4.70 (4H, m), 5.77 (1H, d, J=2 Hz), 7.37 (1H, d, J=2 Hz), 8.61 (1H, s).

Preparation 2

(1) To a suspension of 5-oxo-4,5,6,7-tetrahydropyrazolo[1,5-a]pyrimidine (0.5 g) in tetrahydrofuran (10 ml) was added lithium aluminum hydride (0.277 g) at room temperature. The mixture was stirred at ambient temperature for 30 minutes. To the mixture was added sodium fluoride (1.22 g), and then water (0.394 g) was added dropwise thereto under ice-cooling. The mixture was stirred at 0°-5° C. for 30 minutes and filtered. The filtrate was evaporated to give 4,5,6,7-tetrahydropyrazolo[1,5-a]pyrimidine (257 mg).

IR (Nujol): 3220, 1570, 1460 cm$^{-1}$.

NMR (DMSO-d$_6$, δ): 1.78-2.01 (2H, m), 3.0-3.21 (2H, m), 3.90 (2H, t, J=6 Hz), 5.10 (1H, d, J=2 Hz), 5.86 (1H, br s), 6.97 (1H, d, J=2 Hz).

(2) To acetic anhydride (0.153 ml) was added formic acid (0.077 ml) at 15-20° C. The mixture was stirred at ambient temperature for 30 minutes. To this solution was added 4,5,6,7-tetrahydropyrazolo[1,5-a]pyrimidine (100 mg) under ice-cooling and the mixture was stirred at the same temperature for 1 hour. The reaction mixture was added to a mixture of dichloromethane and aqueous sodium bicarbonate solution. The separated organic layer was dried over magnesium sulfate and evaporated in vacuo to give 4-formyl-4,5,6,7-tetrahydropyrazolo[1,5-a]pyrimidine (79.9 mg).

IR (Nujol): 1670, 1535, 1500, 1450, 1430, 1400 cm$^{-1}$.

NMR (DMSO-d$_6$, δ): 1.97-2.27 (2H, m), 3.62-3.91 (2H, m), 3.97-4.24 (2H, m), 6.22 and 6.48 (1H, each d, J=3 Hz), 7.29 (1H, d, J=3 Hz), 8.19 and 8.77 (1H, each s).

Preparation 3

(1) To a solution of 1-(2-hydroxyethyl)-4-ethoxycarbonyl-5-aminopyrazole (200 g) in a mixture of methylene chloride (2 l) and triethylamine (210 ml) was added dropwise methanesulfonyl chloride (85.5 ml) under ice-cooling. The mixture was stirred for 1 hour at 3°-5° C. The reaction mixture was poured into ice-water (700 ml). The separated organic layer was washed with 1N hydrochloric acid and water, and dried over magnesium sulfate. The solvent was evaporated to give 1-(2-methylsulfonyloxyethyl)-4-ethoxycarbonyl-5-aminopyrazole (270.8 g) as crystals.

IR (Nujol): 3450, 3340, 1680, 1625, 1540 cm$^{-1}$.

NMR (DMSO-d$_6$, δ): 1.20 (3H, t, J=7 Hz), 3.04 (3H, s), 4.03-4.57 (6H, m), 6.28 (2H, br s), 7.47 (1H, s).

(2) A mixture of acetic anhydride (184 ml) and formic acid (93 ml) was stirred for 30 minutes at room temperature. The mixture was cooled at 5° C. with ice-bath and added to 1-(2-methylsulfonyloxyethyl)-4-ethoxycarbonyl-5-aminopyrazole (270 g). The mixture was stirred for 3 hours under ice-cooling. The reaction mixture was evaporated to give crystals. To the crystals was added diisopropyl ether and the mixture was stirred for 1 hour. The crystals were collected by filtration to give 1-(2-methylsulfonyloxyethyl)-4-ethoxycarbonyl-5-formamidopyrazole (291.5 g).

IR (Nujol): 3250, 1720, 1670, 1570, 1530 cm$^{-1}$.

NMR (DMSO-d$_6$, δ): 1.25 (3H, t, J=7 Hz), 3.10 (3H, s), 4.00-4.60 (6H, m), 7.86 (1H, s), 8.24 (1H, br s).

(3) 1-Formyl-2,3-dihydro-7-ethoxycarbonyl-1H-imidazo-[1,2-b]pyrazole was obtained according to a similar manner to that of Preparation 1(3).

IR (Nujol): 1670-1710, 1580, 1520 cm$^{-1}$.

NMR (DMSO-d$_6$, δ): 1.25 (3H, t, J=7 Hz), 4.02-4.60 (6H, m), 7.67 (1H, s), 9.46 (1H, s).

(4) To a suspension of 1-formyl-2,3-dihydro-7-ethoxycarbonyl-1H-imidazo[1,2-b]pyrazole (40 g) in methanol (200 ml) was added conc. hydrochloric acid (31.9 ml) under ice-cooling. The mixture was stirred at room temperature for 2 hours. The reaction mixture was poured into ice-water (300 ml) and adjusted to pH 6.5 with 40% aqueous potassium carbonate solution. The mixture was evaporated to precipitate the crystals. The crystals were collected by filtration to give 2,3-dihydro-7-ethoxycarbonyl-1H-imidazo[1,2-b]pyrazole (33.4 g).

NMR (DMSO-d$_6$, δ): 1.20 (3H, t, J=7 Hz), 3.70-4.27 (6H, m), 6.46 (1H, br s), 7.40 (1H, s).

(5) To a solution of 2,3-dihydro-7-ethoxycarbonyl-1H-imidazo[1,2-b]pyrazole (5 g) in xylene (27 ml) was added dropwise 3.4M solution (27 ml) of sodium bis(2-methoxyethoxy)aluminum hydride in toluene under ice-cooling. The mixture was stirred at room temperature and then stirred at 140° C. for 3.5 hours. The reaction mixture was cooled at 5° C. and poured into a mixture of ice-water (100 ml) and tetrahydrofuran (100 ml). The insoluble material was filtered off and the filtrate was separated. The aqueous layer was extracted with tetrahydrofuran. The organic layer and extract were combined and dried over magnesium sulfate. The solvent was evaporated to give 2,3-dihydro-7-methyl-1H-imidazo[1,2-b]pyrazole (2.04 g).

NMR (DMSO-d$_6$, δ): 1.85 (3H, s), 3.57-4.10 (4H, m), 5.37 (1H, br s), 6.97 (1H, s).

(6) 1-Formyl-2,3-dihydro-7-methyl-1H-imidazo[1,2-b]pyrazole was obtained according to a similar manner to that of Preparation 2(2).

NMR (DMSO-d$_6$, δ): 2.09 (3H, s), 4.05-4.70 (4H, m), 7.17 (1H, s), 8.70 (1H, s).

Preparation 4

(1) To a solution of 2,3-dihydro-1H-imidazo[1,2-b]pyrazole (19 g) in dimethylsulfoxide (95 ml) were added ethyl bromoacetate (20.4 ml) and potassium bicarbonate (30 g) under ice-cooling. The mixture was stirred at room temperature for 4 hours. The reaction mixture was poured into a mixture of ethyl acetate (1.5 l) and water (500 ml). The separated organic layer was washed with water and brine, and dried over magnesium sulfate. The solvent was evaporated and the residue was subjected to column chromatography on silica gel using ethyl acetate as an eluent. Fractions containing the object compound were combined and evaporated in vacuo to give 1-ethoxycarbonylmethyl-2,3-dihydro-1H-imidazo[1,2-b]pyrazole (20.3 g).

IR (Nujol): 3400, 1710-1760, 1570 cm$^{-1}$.

NMR (DMSO-d$_6$, δ): 1.13 (3H, t, J=7 Hz), 3.63-4.30 (6H, m), 4.27 (2H, s), 5.20 (1H, s), 7.07 (1H, s).

(2) To a suspension of lithium aluminum hydride (3.89 g) in tetrahydrofuran (195 ml) was added dropwise a solution of 1-ethoxycarbonylmethyl-2,3-dihydro-1H-imidazo[1,2-b]-pyrazole (20 g) in tetrahydrofuran (100 ml) at room temperature. The mixture was stirred at 50° C. for 1 hour. The reaction mixture was cooled under ice-bath To a mixture were added sodium fluoride (17.2 g) and water (5.5 ml) under ice-cooling. The insoluble material was filtered off and the filtrate was evaporated. The residue was subjected to column chromatography on silica gel using ethyl acetate as an eluent. Fractions containing the object compound were combined and evaporated in vacuo to give 1-(2-hydroxyethyl)-2,3-dihydro-1H-imidazo[1,2-b]pyrazole (5.91 g).

IR (Nujol): 3250-3350, 1560-1570, 1505 cm$^{-1}$.

NMR (DMSO-d$_6$, δ): 3.04 (2H, t, J=5 Hz), 3.43-3.57 (2H, m), 3.57-4.17 (4H, m), 4.69 (1H, t, J=5 Hz), 5.27 (1H, d, J=3 Hz), 7.15 (1H, d, J=3 Hz).

Preparation 5

To a suspension of 62% sodium hydride (1.41 g) in N,N-dimethylformamide (30 ml) was added 4,5,6,7-tetrahydropyrazolo[1,5-a]pyrimidine (4.5 g) under ice-cooling. To this solution was added dropwise methyl iodide (2.27 ml) under ice-cooling, and the mixture was stirred at the same temperature for 1.5 hours. The reaction mixture was poured into ethyl acetate (50 ml), and the resulting precipitate was filtered off. The filtrate was evaporated to give 4-methyl-4,5,6,7-tetrahydropyrazolo[1,5-a]pyrimidine (5.05 g).

NMR (CDCl$_3$, δ): 2.08-2.32 (2H, m), 3.01-3.13 (2H, m), 4.03-4.22 (2H, m], 5.29 (1H, d, J=3 Hz), 7.22 (1H, d, J=3 Hz).

Preparation 6

The following compound was obtained according to a similar manner to that of Preparation 5.
1-Methyl-2,3-dihydro-1H-imidazo[1,2-b]pyrazole NMR (CDCl$_3$, δ): 2.83 (3H, s), 3.52-3.82 (2H, m), 3.93-4.30 (2H, m), 5.29 (1H, d, J=3 Hz), 7.31 (1H, d, J=3 Hz).

Preparation 7

To a solution of benzhydryl 7β-t-butoxycarbonylamino-3-chloromethyl-4-carboxylate (5.76 g) in N,N-dimethylformamide (5.8 ml) was added sodium iodide (1.68 g). After the mixture was stirred at room temperature for 30 minutes, 1-formyl-2,3-dihydro-1H-imidazo[1,2-b]pyrazole (4.6 g) was added thereto. The mixture was stirred at room temperature overnight. The reaction mixture was poured into a mixture of ice water (30 ml) and ethyl acetate (120 ml). The separated organic layer was washed with water and then brine, and dried over magnesium sulfate. The solvent was distilled off and the residue was pulverized with diisopropyl ether and collected by filtration to give benzhydryl 7β-t-butoxycarbonylamino-3-[1-formyl-2,3-dihydro-5-(1H-imidazo[1,2-b]pyrazolio)]methyl-3-cephem-4-carboxylate iodide (7.52 g).

NMR (DMSO-d$_6$, δ): 1.35 (9H, s), 3.47 (2H, br s), 4.07-4.80 (4H, m), 5.12 (1H, d, J=5 Hz), 5.27 (2H, br s), 5.52, 5.62 (1H, dd, J=5 Hz, 8 Hz), 6.47-6.73 (1H, m), 6.87 (1H, s), 7.02-7.57 (10H, m), 7.60-8.08 (1H, m), 8.25 (1H, d, J=3 Hz), 8.09 (1H, s).

Preparation 8

The following compounds were obtained according to a similar manner to that of Preparation 7.
(1) Benzhydryl 7β-t-butoxycarbonylamino-3-(4-methyl-4,5,6,7-tetrahydro-1-pyrazolo[1,5-a]pyrimidinio)-methyl-3-cephem-4-carboxylate iodide
IR (Nujol): 3300, 1775, 1705, 1615 cm$^{-1}$.

NMR (DMSO-d$_6$, δ): 1.44 (9H, s), 1.82-2.22 (2H, m), 2.99 (3H, s), 3.23-4.07 (6H, m), 5.08-5.22 (3H, m), 5.55 (1H, dd, J=8, 5 Hz), 6.13 (1H, d, J=3 Hz), 6.93 (1H, s), 7.13-7.51 (10H, m), 7.85 (1H, d, J=8 Hz), 8.02 (1H, d, J=3 Hz).

(2) Benzhydryl 7β-t-butoxycarbonylamino-3-(4-formyl-4,5,6,7-tetrahydro-1-pyrazolo[1,5-a]pyrimidinio)-methyl-3-cephem-4-carboxylate iodide
IR (Nujol): 1785, 1705, 1560 cm$^{-1}$.

NMR (DMSO-d$_6$, δ): 1.43 (9H, s), 1.88-2.27 (2H, m), 3.46 (2H, br s), 3.55-4.22 (4H, m), 5.15 (1H, d, J=5 Hz), 5.43 (2H, br s), 5.58 (1H, dd, J=8 Hz, 5 Hz), 6.91 (1H, s), 7.01 (1H, d, J=3 Hz), 7.13-7.55 (10H, m), 7.94 (1H, d, J=8 Hz), 8.32 (1H, d, J=3 Hz), 8.43 and 9.04 (1H, each s).

(3) Benzhydryl 7β-t-butoxycarbonylamino-3-(5-oxo-4,5,6,7-tetrahydro-1-pyrazolo[1,5-a]pyrimidinio)-methyl-3-cephem-4-carboxylate iodide
IR (Nujol): 1780, 1710, 1590 cm$^{-1}$.

NMR (DMSO-d$_6$, δ): 1.43 (9H, s), 2.76 (2H, t, J=8 Hz), 3.43 (2H, br s), 4.13 (2H, J=8 Hz), 5.12 (1H, d, J=5 Hz), 5.38 (2H, br s), 5.58 (1H, dd, J=8, 5 Hz), 6.18 (1H, d, J=3 Hz), 6.91 (1H, s), 7.12-7.53 (10H, m), 7.93 (1H, d, J=8 Hz), 8.25 (1H, d, J=3 Hz).

(4) Benzhydryl 7β-t-butoxycarbonylamino-3-[1-(2-hydroxyethyl)-2,3-dihydro-5-(1H-imidazo[1,2-b]pyrazolio)]methyl-3-cephem-4-carboxylate iodide
IR (Nujol): 3400, 1780, 1670 cm$^{-1}$.

NMR (DMSO-d$_6$, δ): 3.40-4.00 (4H, m), 4.07-4.70 (4H, m), 5.01-5.50 (4H, m), 5.20 (1H, d, J=5 Hz), 5.60 (1H, dd, J=5 Hz, 8 Hz), 6.01 (1H, d, J=3 Hz), 6.90 (1H, s), 7.02-7.49 (10H, m), 8.10 (1H, d, J=3 Hz).

(5) Benzhydryl 7β-t-butoxycarbonylamino-3-[1-formyl-2,3-dihydro-7-methyl-5-(1H-imidazo[1,2-b]pyrazolio)]methyl-3-cephem-4-carboxylate iodide
NMR (DMSO-d$_6$, δ): 1.43 (9H, s), 2.20 (3H, s), 3.22 (2H, br s), 4.07-4.80 (4H, m), 5.03-5.37 (3H, m), 5.63 (1H, dd, J=5 Hz, 8 Hz), 6.94 (1H, s), 7.10-7.63 (10H, m), 8.15 (1H, s), 8.90 (1H, br s).

(6) Benzhydryl 7β-t-butoxycarbonylamino-3-[1-methyl-2,3-dihydro-5-(1H-imidazo[1,2-b]pyrazolio)]methyl-3-cephem-4-carboxylate iodide
NMR (DMSO-d$_6$, δ): 1.38 (9H, s), 2.90 (3H, s), 3.30-3.67 (2H, m), 3.72-4.10 (4H, m), 4.90-5.10 (2H, m), 5.13 (1H, d, J=5 Hz), 5.54 (1H, dd, J=5 Hz, 8 Hz), 6.02 (1H, d, J=3 Hz), 6.89 (1H, s), 7.07-7.53 (10H, m), 8.05 (1H, d, J=3 Hz).

(7) Benzhydryl 7β-t-butoxycarbonylamino-3-(4-formyl-6-formyloxy-4,5,6,7-tetrahydro-1-pyrazolo[1,5-a]pyrimidinio)-methyl-3-cephem-4-carboxylate iodide
IR (Nujol): 1780, 1710 cm$^{-1}$.

NMR (DMSO-d$_6$, δ): 1.43 (9H, s), 3.2-3.8 (3H, m), 4.1-4.6 (2H, m), 5.14 (1H, d, J=5 Hz), 5.40 (2H, s), 5.60 (1H, dd, J=8 Hz, 5 Hz), 6.86 (1H, s), 7.06 (1H, d, J=3 Hz), 7.2-7.6 (10H, m), 7.93 (1H, d, J=8 Hz), 8.17 (1H, d, J=3 Hz), 8.20 (1H, s), 8.86 (1H, s).

(8) Benzhydryl 7β-t-butoxycarbonylamino-3-[1-(2-formamidoethyl)-2,3-dihydro-5-(1H-imidazo[1,2-b]pyrazolio)]methyl-3-cephem-4-carboxylate iodide
IR (Nujol): 1780, 1710, 1670, 1610, 1520 cm$^{-1}$.

NMR (DMSO-d$_6$, δ): 1.40 (9H, s), 3.10-3.60 (6H, m), 3.82-4.17 (4H, m), 4.87-5.13 (2H, m), 5.16 (1H, d, J=5 Hz), 5.58 (1H, dd, J=5 Hz, 8 Hz), 5.99 (1H, d, J=2 Hz), 6.93 (1H, s), 7.10-7.53 (10H, m), 7.98 (1H, s), 8.07 (1H, d, J=2 Hz).

(9) Benzhydryl 7β-t-butoxycarbonylamino-3-[1-formyl-7-methylthio-2,3-dihydro-5-(1H-imiazo[1,2-b]pyrazolio)]methyl-3-cephem-4-caroxylate iodide
IR (Nujol) 1780, 1670, 1510 cm$^{-1}$.

Preparation 9

To a suspension of benzhydryl 7β-t-butoxycarbonylamino-3-[1-formyl-2,3-dihydro-5-(1H-imidazo[1,2-b]pyrazolio)]methyl-3-cephem-4-carboxylate iodide (7.5 g) in a mixture of anisole and methylene chloride was added dropwise trifluoroacetic acid (15 ml) under ice-cooling. The mixture was stirred at room temperature for 1.5 hours. The reaction mixture was poured into a mixture of diisopropyl ether (115 ml) and ethyl acetate (115 ml). The resultant powder was collected by filtration and washed with diisopropyl ether and dried over phosphorus pentoxide in vacuo to give 7β-amino-3-[1-formyl-2,3-dihydro-5-(1H-imidazo[1,2-b]pyrazolio)]methyl-3-cephem-4-carboxylate bis(trifluoroacetate) (6.6 g).

Preparation 10

The following compounds were obtained according to a similar manner to that of Preparation 9.

(1) 7β-Amino-3-(4-methyl-4,5,6,7-tetrahydro-1-pyrazolo[1,5-a]pyrimidinio)methyl-3-cephem-4-carboxylate bis(trifluoroacetate)

IR (Nujol): 1780, 1665, 1620 cm$^{-1}$.

NMR (DMSO-d$_6$, δ): 1.84–2.29 (2H, m), 3.03 (3H, m), 3.13–3.55 (4H, m), 3.82–4.22 (2H, m), 5.13–5.33 (4H, m), 6.17 (1H, d, J=3 Hz), 8.05 (1H, d, J=3 Hz).

(2) 7β-Amino-3-(4-formyl-4,5,6,7-tetrahydro-1-pyrazolo-[1,5-a]pyrimidinio)methyl-3-cephem-4-carboxylate bis(trifluoroacetate)

IR (Nujol): 3350, 1780, 1650 cm$^{-1}$.

NMR (DMSO-d$_6$, δ): 2.04–2.45 (2H, m), 3.49 (2H, br s), 3.72–4.38 (4H, m), 5.22 (2H, br s), 5.49 (2H, br s), 7.07 (1H, br s), 8.35 (1H, d, J=3 Hz), 8.47 and 9.07 (1H, each s).

(3) 7β-Amino-3-(5-oxo-4,5,6,7-tetrahydro-1-pyrazolo-[1,5-a]pyrimidinio)methyl-3-cephem-4-carboxylate bis(trifluoroacetate)

IR (Nujol): 1775, 1680, 1590 cm$^{-1}$.

NMR (DMSO-d$_6$, δ): 2.99 (2H, t, J=7 Hz), 3.46 (2H, br s), 4.43 (2H, t, J=7 Hz), 5.19 (2H, br s), 5.44 (2H, br s), 6.23 (1H, d, J=3 Hz), 8.27 (1H, J=3 Hz).

(4) 7β-Amino-3-[1 (2-hydroxyethyl)-2,3-dihydro-5-(1H-imidazo[1,2-b]pyrazolio)]methyl-3-cephem-4-carboxylate bis(trifluoroacetate)

IR (Nujol): 3400, 1775, 1650, 1510 cm$^{-1}$.

NMR (D$_2$O, δ): 3.37–3.90 (4H, m), 3.97–4.53 (4H, m), 4.97–5.40 (4H, m), 5.91 (1H, d, J=3 Hz), 7.96 (1H, d, J=3 Hz).

(5) 7β-Amino-3-[1-formyl-2,3-dihydro-7-methyl-5-(1H-imidazo[1,2-b]pyrazolio)]methyl-3-cephem-4-carboxylate bis(trifluoroacetate)

NMR (DMSO-d$_6$, δ): 2.20 (3H, s), 3.55 (2H, br s), 4.33–4.73 (4H, m), 5.02–5.43 (4H, m), 8.20 (1H, s), 8.87 (1H, br s)

(6) 7β-Amino-3-[1-methyl-2,3-dihydro-5-(1H-imidazo-[1,2-b]pyrazolio)]methyl-3-cephem-4-carboxylate bis(trifluoroacetate)

NMR (D$_2$O—NaHCO$_3$, δ): 2.87 (3H, s), 3.12, 3.40 (2H, ABq, J=18 Hz, 24 Hz), 3.63–4.30 (4H, m), 4.73–5.10 (4H, m), 5.75 (1H, d, J=3 Hz), 7.82 (1H, d, J=3 Hz).

(7) 7δ-Amino-3-(4-formyl-6-formyloxy-4,5,6,7-tetrahydro-1-pyrazolo[1,5-a]pyrimidinio)methyl-3-cephem-4-carboxylate bis(trifluoroacetate)

IR (Nujol): 1780, 1700 cm$^{-1}$.

NMR (DMSO-d$_6$, δ): 3.52 (2H, br s), 3.2–3.8 (3H, m), 4.1–4.6 (2H, m), 5.26 (2H, m), 5.52 (2H, s), 7.15 (1H, d, J=3 Hz), 8.22(1H, d, J=3 Hz), 8.50 (1H, s), 9.20 (1H, s).

(8) 7β-Amino-3-[1-(2-formamidoethyl)-2,3-dihydro-5-(1H-imidazo[1,2-b]pyrazolio)]methyl-3-cephem-4-carboxylate bis(trifluoroacetate)

NMR (D$_2$O-NaHCO$_3$, δ): 3.17, 3.46 (2H, ABq, J=18 Hz, 26 Hz), 3.50 (4H, s), 3.95–4.50 (4H, m), 4.86, 5.03 (2H, ABq, J=11 Hz, 16 Hz), 5.06 (1H, d, J=5 Hz), 5.85 (1H, d, J=2 Hz), 7.92 (1H, d, J=2 Hz), 8.01 (1H, s).

(9) 7β-Amino-3-[1-formyl-7-methylthio-2,3-dihydro-5-(1H-imidazo[1,2-b]pyrazolio)]methyl-3-cephem-4-carboxylate bis(trifluoroacetate)

NMR (D$_2$O, δ): 2.29, 2.32 (total 3H, each s), 3.20–3.63 (2H, m), 4.03–4.60 (4H, m), 4.87–5.45 (4H, m), 8.05 (1H, s), 8.44 (1H, s).

Preparation 11

To a suspension of 7β-amino-3-[1-formyl-2,3-dihydro- 5-(1H-imidazo[1,2-b]pyrazolio)]methyl-3-cephem-4-carboxylate bis(trifluoroacetate) (6.5 g) in methanol (38 ml) was added concentrated hydrochloric acid (3.3 ml). The mixture was stirred at room temperature for 2 hours. The reaction mixture was added dropwise ethyl acetate (330 ml). The resultant powder was collected by filtration, washed with diisopropyl ether and dried over phosphorus pentoxide in vacuo to give 7β-amino-3-[2,3-dihydro-5-(1H-imidazo[1,2-b]pyrazolio)]methyl-3-cephem-4-carboxylate trihydrochloride (3.35 g).

NMR (D$_2$O, δ): 3.37 (1H, d, J=18 Hz), 3.63 (1H, d, J=18 Hz), 3.93–4.47 (4H, m), 5.12 (2H, s), 5.14 (1H, d, J=5 Hz), 5.30 (1H, d, J=5 Hz), 5.86 (1H, d, J=2 Hz), 7.92 (1H, d, J=2 Hz).

Preparation 12

The following compounds were obtained according to a similar manner to that of Preparation 11.

(1) 7δ-Amino-3-(4,5,6,7-tetrahydro-1-pyrazolo[1,5-a]pyrimidinio)methyl-3-cephem-4-carboxylate trihydrochloride IR (Nujol): 3350, 1780, 1700, 1620 cm$^{-1}$.

NMR (DMSO$_6$, δ): 1.87–2.17 (2H, m), 3.27 (2H, br s), 3.36–3.55 (2H, m), 3.85–4.17 (2H, m), 5.23 (2H, br s), 5.29 (2H, br s), 5.76 (1H, d, J=3 Hz), 8.08 (1H, d, J=3 Hz).

(2) 7β-Amino-3-[2,3-dihydro-7-methyl-5-(1H-imidazo-[1,2-b]pyrazolio)]methyl-3-cephem-4-carboxylate trihydrochloride NMR (D$_2$O—NaHCO$_3$, δ): 1.59 (3H, s), 3.23, 3.50 (2H, ABq, J=18 Hz, 24 Hz), 3.93–4.30 (4H, m), 4.80–5.27 (4H, m), 7.73 (1H, s).

(3) 7β-Amino-3-[7-methylthio-2,3-dihydro-5-(1H-imidazo-[ 1,2-b]pyrazolio)]methyl-3-cephem-4-carboxylate trihydrochloride IR (Nujol): 1785, 1710, 1595 cm$^{-1}$.

NMR (D$_2$O—NaHCO$_3$, δ): 2.31 (3H, s), 3.23, 3.53 (2H, ABq, J=18 Hz, 26 Hz), 3.93–4.40 (4H, m), 4.77–5.20 (2H, m), 4.99 (1H, d, J=5 Hz), 8.02 (1H, s).

Preparation 13

5-Aminopyrazole (10 g) and 1,3-dibromopropane (13.4 ml) were added to 1,4-dioxane (20 ml) under stirring at ambient temperature. Triethylamine (40.1 ml) was added thereto. The mixture was refluxed under stirring for 4 hours. The reaction mixture was cooled to 0°–5° C. in an ice-bath and stirred for 30 minutes. An insoluble material was filtered off, and the filtrate was evaporated under reduced pressure to give 4,5,6,7-tetrahydropyrazolo[1,5-a]pyrimidine (5.1 g).

IR (Nujol): 3220, 1570, 1460 cm$^{-1}$.

Preparation 14

(1) The following compound was obtained according to a similar manner to that of Preparation 13.

6-Hydroxy-4,5,6,7-tetrahydropyrazolo[1,5-a]pyrimidine

IR (Nujol): 3350, 3110, 1600, 1460, 1380 cm$^{-1}$.

NMR (DMSO-d$_6$, δ): 2.90–3.30 (2H, m), 3.60–3.80 (1H, m), 4.00–4.20 (2H, m), 5.15 (1H, d, J=1.9 Hz), 5.23 (1H, d, J=3.8 Hz), 5.93 (1H, s), 7.05 (1H, d, J=1.9 Hz).

(2) The following compound was obtained by reacting 6-hydroxy-4,5,6,7-tetrahydropyrazolo[1,5-a]pyrimidine according to a similar manner to that of Preparation 2(2).

4-Formyl-6-formyloxy-4,5,6,7-tetrahydropyrazolo-[1,5-a]pyrimidine

NMR (CDCl$_3$, δ): 3.30–4.80 (4H, m), 5.50–5.80 (1H, m), 6.01 and 6.67 (each d, 1H, J=3 Hz), 7.41 (1H, d, J=3 Hz), 7.96 (1H, s), 8.12 and 8.72 (1H, each s).

Preparation 15

(1) To a solution of 1-methoxycarbonylmethyl-2,3-dihydro-1H-imidazo[1,2-b]pyrazole (27 g) in ethanol (135 ml) was added 28% ammonium solution (100 ml). The mixture was stirred overnight at room temperature. The insoluble material was filtered off and the filtrate was evaporated to precipitate the crystals. The crystals were collected by filtration to give 1-carbamoylmethyl-2,3-dihydro-1H-imidazo[1,2-b]pyrazole (6 g).

NMR (DMSO-$d_6$, $\delta$): 3.06 (2H, s), 3.65-3.91 (2H, m), 3.91-4.21 (2H, m), 5.28 (1H, d, J=2 Hz), 7.16 (1H, d, J=2 Hz), 6.87-7.67 (2H, br).

(2) To a suspension of lithium aluminum hydride (2.84 g) in tetrahydrofuran (70 ml) was added dropwise a solution of 1-carbamoylmethyl-2,3-dihydro-1H-imidazo[1,2-b]pyrazole (6.2 g) in tetrahydrofuran (30 ml) at room temperature. The mixture was refluxed for 4 hours and cooled with ice-bath. Sodium fluoride (12.5 g) and water (4 ml) were added to the mixture under cooling. The insoluble material was filtered off and the filtrate was evaporated to give 1-(2-aminoethyl)-2,3-dihydro-1H-imidazo-1,2-b]pyrazole (4.2 g).

NMR (DMSO-$d_6$, $\delta$): 2.42-3.20 (4H, m), 3.40-4.20 (4H, m), 5.25 (1H, s), 7.14 (1H, s).

(3) A mixture of acetic anhydride (4.96 ml) and formic acid (2.51 ml) was stirred for 45 minutes at room temperature. The mixture was cooled to 5° C., and 1-(2-aminoethyl)-2,3-dihydro-1H-imidazo[1,2-b]pyrazole (4.0 g) was added to the mixture. The mixture was stirred for an hour under ice-cooling. The reaction mixture was evaporated and the residue was subjected to column chromatography on silica gel using a mixture of chloroform and methanol (9:1) as an eluent. Fractions containing the object compound were combined and evaporated to give 1-(2-formamidoethyl)-2,3-dihydro-1H-imidazo[1,2-b]pyrazole (2.6 g) as crystals.

NMR (DMSO-$d_6$, $\delta$): 2.80-3.50 (4H, m), 3.58-3.87 (2H, m), 3.87-4.7 (2H, m), 5.29 (1H, d, J=2 Hz), 7.18 (1H, d, J=2 Hz), 8.03 (1H, s).

Preparation 16

(1) To a mixture of 3-dimethylamino-2-methylthioacrylonitrile (5 g) and 2-hydrazinoethanol (2.68 g) in ethanol (50 ml) was added conc. hydrochloric acid (2.93 ml) under ice-cooling. The mixture was refluxed for 3 hours. The reaction mixture was evaporated to remove the solvent. The residue was adjusted to pH 7 with a saturated aqueous solution of sodium bicarbonate and extracted with a mixture of tetrahydrofuran and ethyl acetate. The organic layer was dried over magnesium sulfate. The solvent was removed in vacuo and the residue was subjected to column chromatography on silica gel using ethyl acetate as an eluent. Fractions containing the object compound were combined and evaporated to give 1-(2-hydroxyethyl)-4-methylthio-5-aminopyrazole (2.4 g).

IR (Nujol): 3400, 1620, 1540, 1515, 1460 cm$^{-1}$.

NMR (DMSO-$d_6$, $\delta$): 2.01 (3H, s), 3.61 (2H, t, J=5 Hz), 3.83 (2H, t, J=5 Hz), 4.81 (1H, t, J=5 Hz), 5.19 (2H, br s), 7.07 (1H, s).

(2) The following compound was obtained according to a similar manner to that of Preparation 1(1).

1-(2-Hydroxyethyl)-4-methylthio-5-formamidopyrazole

NMR (DMSO-$d_6$, $\delta$): 2.21, 2.24 (total 3H, each s), 3.63-3.69 (2H, m), 3.95, 4.04 (total 2H, each t, J=6 Hz), 7.55, 7.60 (total 1H, each s), 8.17, 8.31 (total 1H, each s).

(3) The following compound was obtained according to a similar manner to that of Preparation 1(2).

1-(2-Methylsulfonyloxyethyl)-4-methylthio-5-formamidopyrazole

NMR (DMSO-$d_6$, $\delta$): 2.22, 2.24 (total 3H, each s), 3.02, 3.07 (total 3H, each s), 4.24, 4.34 (total 2H, each t, J=5 Hz), 4.50 (2H, t, J=5 Hz), 7.63 (1H, s), 8.33 (1H, s), 10.1 (1H, s).

(4) The following compound was obtained according to a similar manner to that of Preparation 1(3).

1-Formyl-7-methylthio-2,3-dihydro-1H-imidazo-[1,2-b]pyrazole

IR (Nujol): 1665, 1560, 1510 cm$^{-1}$.

NMR (DMSO-$d_6$, $\delta$): 2.25, 4.13-4.47 (4H, m), 7.39 (1H, s), 9.03 (1H, s).

Preparation 17

The following compound was obtained by reacting 7$\delta$-amino-3-(4-formyl-6-formyloxy-4,5,6,7-tetrahydro-1-pyrazolo[1,5-a]pyrimidinio)methyl-3-cephem-4-carboxylate bis(trifluoroacetate) according to a similar manner to that of Preparation 11.

7$\delta$-Amino-3-(6-hydroxy-4,5,6,7-tetrahydro-1-pyrazolo[1,5-a]pyrimidinio)methyl-3-cephem-4-carboxylate trihydrochloride IR (Nujol): 3250, 1780, 1620, 1230 cm$^{-1}$.

NMR (DMSO-$d_6$, $\delta$): 3.40 (2H, br s), 3.20 (1H, m), 3.66 (2H, m), 4.1-4.6 (2H, m), 5.16 (2H, m), 5.23 (2H, s), 5.85 (1H, d, J=3 Hz), 8.60 (1H, d, J=3 Hz).

Preparation 18

A solution of 7$\beta$-amino-3-[2,3-dihydro-5-(1H-imidazo-[1,2-b]pyrazolio)]methyl-3-cephem-4-carboxylate trihydrochloride (87 g) in water (348 ml) was subjected to column chromatography on HP-20 (609 ml), and the elution was carried out with water. The fractions containing the objective compound were combined and isopropyl alcohol (3 l) was added dropwise thereto under ice-cooling. The resulting precipitate was collected by filtration to give 7$\beta$-amino-3-[2,3-dihydro-5-(1H-imidazo[1,2-b]pyrazolio)]-methyl-3-cephem-4-carboxylate hydrochloride (48.32 g) as crystals.

IR (Nujol): 1780, 1640, 1590 cm$^{-1}$.

NMR (D$_2$O, $\delta$): 3.35 and 3.62 (2H, ABq, J=17 Hz), 3.98-4.45 (4H, m), 5.07 (2H, s), 5.16 (1H, d, J=5 Hz), 5.29 (1H, d, J=5 Hz), 5.86 (1H, d, J=3 Hz), 7.92 (1H, d, J=3 Hz).

Preparation 19

The following compound was obtained according to a similar manner to that of Preparation 18.

7$\beta$-Amino-3-(4,5,6,7-tetrahydro-1-pyrazolo[1,5-a]pyrimidinio)methyl-3-cephem-4-carboxylate hydrochloride (crystal)

IR (Nujol): 1790, 1640, 1600 cm$^{-1}$.

NMR (D$_2$O, $\delta$): 1.92-2.22 (2H, m), 3.11-3.53 (4H, m), 3.95-4.13 (2H, m), 5.06 and 5.21 (2H, ABq, J=15 Hz), 5.11 (1H, d, J=5 Hz), 5.22 (1H, d, J=5 Hz), 5.82 (1H, d, J=3 Hz), 7.74 (1H, d, J=3 Hz).

EXAMPLE 1

To a solution of 7$\beta$-amino-3-[2,3-dihydro-5-(1H-imidazo[1,2-b]pyrazolio)]methyl-3-cephem-4-carboxylate trihydrochloride (0.7 g), N-(trimethylsilyl)acetamide (2.13 g) and methylene chloride (14 ml) were added 2-(5-amino-1,2,4-thiadiazol-3-yl)-2-(1-carboxy-1-methylethoxyimino)acetic methanesulfonic anhydride (syn isomer) (0.57 g) under ice-cooling. The mixture was stirred at room temperature for 2 hours. The reaction mixture was poured into water (10 ml) and adjusted to pH 6 with a saturated aqueous solution of sodium bicarbonate. The separated aqueous layer was adjusted to pH 2.5 with 1N hydrochloric acid and the insoluble material was filtered off. The aqueous solution was subjected to column chromatography on "Diaion HP-20" (Trademark: manufactured by Mitsubishi Chemical Industries) using 5% aqueous isopropyl alcohol as an eluent. Fractions containing the object compound were combined and evaporated in vacuo to remove isopropyl alcohol. The residue was lyophilized to give 7β-[2-(5-amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate (syn isomer) (0.39 g).

IR (Nujol): 3300, 1770, 1670, 1600, 1520 cm$^{-1}$.

NMR (D$_2$O—NaHCO$_3$, δ): 1.53 (6H, s), 3.21 (1H, d, J=18 Hz), 3.50 (1H, d, J=18 Hz), 3.93–4.35 (4H, m), 4.90 (1H, d, J=13 Hz), 5.10 (1H, d, J=13 Hz), 5.22 (1H, d, J=5 Hz), 5.70–5.92 (2H, m), 7.89 (1H, d, J=2 Hz).

EXAMPLE 2

A mixture of N,N-dimethylformamide (0.26 ml), ethyl acetate (0.7 ml) and phosphorus oxychloride (0.3 ml) was stirred for 30 minutes under ice-cooling and tetrahydrofuran (6 ml) was added thereto. 2-(2-Formamidothiazol-4-yl)-2-methoxyiminoacetic acid (syn isomer) (0.64 g) was added to the mixture under ice-cooling, and the mixture was stirred for 1 hour at 3° to 5° C. to produce an activated acid solution. On the other hand, 7β-amino-3-[2,3-dihydro-5-(1H-imidazo[1,2-b]pyrazolio)]methyl-3-cephem-4-carboxylate trihydrochloride (1.2 g) was dissolved in a solution of N-trimethylsilylacetamide (3.66 g) in methylene chloride (25 ml). To the solution was added the above activated acid solution at −20° C. and the mixture was stirred at −10° to 0° C. for 2 hours. The reaction mixture was poured into ethyl acetate (25 ml) and the resultant powder was collected by filtration and washed with diisopropyl ether and dried over magnesium sulfate in vacuo to give 7β-[2-(2-formamidothiazol-4-yl)-2-methoxyiminoacetamido]-3-[2,3-dihydro-5-(1H-imidazo-[1,2-b]pyrazolio)]methyl-3-cephem-4-carboxylate (syn isomer) (3.4 g).

EXAMPLE 3

To a solution of 7β-amino-3-[1-methyl-2,3-dihydro-5-(1H-imidazo[1,2-b]pyrazolio)]methyl-3-cephem-4-carboxylate bis(trifluoroacetate) (1 g), N-(trimethylsilyl)acetamide (2.45 g) and methylene chloride (20 ml) was added 2-(5-amino-1,2,4-thiadiazol-3-yl)-2-(1-carboxy-1-methyl ethoxyimino)acetic methanesulfonic anhydride (syn isomer) (0.66 g) under ice-cooling. The mixture was stirred at 10° C. for 2 hours. The reaction mixture was poured into ethyl acetate (200 ml). The resultant powder was collected by filtration and dissolved in water, and the solution was adjusted to pH 2.5 with a saturated sodium bicarbonate solution. The solution was subjected to column chromatography on HP-20 using 5% aqueous isopropyl alcohol as an eluent. Fractions containing the object compound were combined and evaporated to remove isopropyl alcohol and the residue was lyophilized to give 7β-[1-(5-amino-1,2,4-thiadiazol-3-yl)-2-(1-carboxy-1-methylethoxyimino)acetamido]-3-[1-methyl-2,3-dihydro-5-(1H-imidazo[1,2-b]pyrazolio)]methyl-3-cephem-4-carboxylate (syn isomer) (0.27 g).

IR (Nujol): 3250, 1770, 1670 cm$^{-1}$.

NMR (D$_2$O—NaHCO$_3$, δ): 1.57 (6H, s), 2.98 (3H, s), 3.21, 3.50 (2H, ABq, J=18 Hz, 26 Hz), 3.83–4.40 (4H, m), 4.80–5.10 (2H, m), 5.23 (1H, d, J=5 Hz), 5.83 (1H, d, J=5 Hz), 5.83 (1H, d, J=3 Hz), 7.90 (1H, d, J=3 Hz).

EXAMPLE 4

To a solution of 7β-amino-3-(5-oxo-4,5,6,7-tetrahydro-1-pyrazolo[1,5-a]pyrimidinio)methyl-3-cephem-4-carboxylate bis(trifluoroacetate) (1.5 g) in a mixture of tetrahydrofuran (40 ml) and water (20 ml) was added N,N-dimethylformamide solvate (1.02 g) of 1-[2-(2-aminothiazol-4-yl)-2-methoxyiminoacetyl]-1H-benzotriazol-3-oxide at ambient temperature. The mixture was stirred for 4 hours at pH 7. The solution was adjusted to pH 2 with 1N hydrochloric acid, washed with ethyl acetate five times and evaporated in vacuo to remove ethyl acetate. The solution was subjected to column chromatography on HP-20 and the elution was carried out with 5% aqueous isopropyl alcohol. The objective fraction was collected and lyophilized to give 7β-[2-(2-aminothiazol-4-yl)-2-methoxyiminoacetamido]-3-(5-oxo-4,5,6,7-tetrahydro-1-pyrazolo[1,5-a]pyrimidinio)methyl-3-cephem-4-carboxylate (syn isomer) (261 mg).

IR (Nujol): 3300, 1765, 1700, 1660 cm$^{-1}$.

NMR (D$_2$O, δ): 3.03 (2H, t, J=7 Hz), 3.19 and 3.51 (2H, ABq, J=18 Hz), 3.97 (3H, s), 4.49 (2H, t, J=7 Hz), 5.11 and 5.35 (2H, ABq, J=15 Hz), 5.22 (1H, d, J=5 Hz), 5.82 (1H, d, J=5 Hz), 6.17 (1H, d, J=3 Hz), 6.96 (1H, s), 8.03 (1H, d, J=3 Hz).

EXAMPLE 5

The following compounds were obtained according to similar manners to those of Examples 1–4.

(1)  7β-[2-(5-Amino-1,2,4-thiadiazol-3-yl)-2-methoxyiminoacetamido]-3-[2,3-dihydro-5-(1H-imidazo[1,2-b]pyrazolio)]methyl-3-cephem-4-carboxylate (syn isomer)

IR (Nujol): 3250, 1670, 1600, 1520 cm$^{-1}$.

NMR (D$_2$O, δ): 3.21 (1H, d, J=18 Hz), 3.50 (1H, d, J=18 Hz), 4.06 (3H, s), 3.87–4.37 (4H, m), 4.90 (1H, d, J=13 Hz), 5.13 (1H, d, J=13 Hz), 5.21 (1H, d, J=5 Hz), 5.82 (1H, d, J=3 Hz), 5.85 (1H, d, J=5 Hz), 7.89 (1H, d, J=3 Hz).

(2)  7β-[2-(5-Amino-1,2,4-thiadiazol-3-yl)-2-allyloxyiminoacetamido]-3-[2,3-dihydro-5-(1H-imidazo[1,2-b]pyrazolio)]methyl-3-cephem-4-carboxylate (syn isomer)

IR (Nujol): 3300, 1770, 1670, 1600, 1520 cm$^{-1}$.

NMR (D$_2$O, δ): 3.20 (1H, d, J=18 Hz), 3.50 (1H, d, J=18 Hz), 3.95–4.47 (4H, m), 4.70–4.88 (2H, m), 4.93–5.60 (4H, m), 5.21 (1H, d, J=5 Hz), 5.82 (1H, d, J=3 Hz), 5.70–6.35 (2H, m), 7.89 (1H, d, J=3 Hz).

(3)  7β-[2-(2-Formamidothiazol-4-yl)-2-methoxyiminoacetamido]-3-(4-methyl-4,5,6,7-tetrahydro-1-pyrazolo-[1,5-a]pyrimidinio)methyl-3-cephem-4-carboxylate (syn isomer)

IR (Nujol): 3200, 1765, 1655, 1620 cm$^{-1}$.

NMR (DMSO-d$_6$, δ): 1.96–2.23 (2H, m), 2.97 (3H, m), 3.13–3.44 (4H, m), 3.85 (3H, s), 3.88–4.10 (2H, m), 5.18 (1H, d, J=5 Hz), 5.20 (2H, br s), 6.12 (1H, d, J=3 Hz), 7.33 (1H, s), 8.08 (1H, d, J=3 Hz), 8.43 (1H, s), 9.60 (1H, d, J=8 Hz).

(4) 7β-[2-(5-Amino-1,2,4-thiadiazol-3-yl)-2-(1-carboxy-1-methylethoxyimino)acetamido]-3-(4-methyl- 4,5,6,7-tetrahydro-1-pyrazolo[1,5-a]pyrimidinio)-methyl-3-cephem-4-carboxylate (syn isomer)

IR (Nujol): 3250, 1760, 1660, 1620 cm$^{-1}$.

NMR (D$_2$O+NaHCO$_3$, δ): 1.54 (6H, s), 2.01–2.33 (2H, m), 3.00 (3H, s), 3.14–3.47 (4H, m), 3.88–4.15 (2H, m), 4.88 and 5.19 (2H, ABq, J=16 Hz), 5.18 (1H, d, J=5 Hz), 5.82 (1H, d, J=5 Hz), 5.88 (1H, d, J=3 Hz), 7.77 (1H, d, J=3 Hz).

(5) 7β-[2-(5-Amino-1,2,4-thiadiazol-3-yl)-2-allyloxyiminoacetamido]-3-(4-methyl-4,5,6,7-tetrahydro-1-pyrazolo[1,5-a]pyrimidinio)methyl-3-cephem-4-carboxylate (syn isomer)

IR (Nujol): 3300, 1760, 1670, 1615 cm$^{-1}$.

NMR (D$_2$O, δ): 2.03–2.32 (2H, m), 2.97 (3H, s), 3.07–3.28 (4H, m), 3.82–4.18 (2H, m), 4.77 (2H, d, J=6 Hz), 5.05–5.47 (4H, m), 5.17 (1H, d, J=5 Hz), 5.83 (1H, d, J=5 Hz), 5.84–6.28 (1H, m), 5.87 (1H, d, J=3 Hz), 7.77 (1H, d, J=3 Hz).

(6) 7β-[2-(5-Amino-1,2,4-thiadiazol-3-yl)-2-methoxyiminoacetamido]-3-(4,5,6,7-tetrahydro-1-pyrazolo[1,5-a]pyrimidinio)methyl-3-cephem-4-carboxylate (syn isomer)

IR (Nujol): 3200, 1760, 1650, 1605 cm$^{-1}$.

NMR (D$_2$O, δ): 1.93–2.33 (2H, m), 3.05–3.49 (4H, m), 3.92–4.18 (2H, m), 4.08 (3H, s), 4.85 and 5.23 (2H, ABq, J=15 Hz), 5.18 (1H, d, J=5 Hz), 5.82 (1H, d, J=3 Hz), 5.84 (1H, d, J=5 Hz), 7.73 (1H, d, J=3 Hz).

(7) 7β-[2-(5-Amino-1,2,4-thiadiazol-3-yl)-2-allyloxyiminoacetamido]-3-(4,5,6,7-tetrahydro-1-pyrazolo[1,5-a]pyrimidinio)methyl-3-cephem-4-carboxylate (syn isomer)

IR (Nujol): 3250, 1760, 1660, 1600 cm$^{-1}$.

NMR (D$_2$O, δ): 1.93–2.32 (2H, m), 3.02–3.48 (4H, m), 3.88–4.18 (2H, m), 4.76 (2H, d, J=6 Hz), 4.94–5.44 (4H, m), 5.18 (1H, d, J=5 Hz), 5.78 (1H, d, J=3 Hz), 5.82 (1H, d, J=5 Hz), 5.83–6.27 (1H, m), 7.83 (1H, d, J=3 Hz).

(8) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate (syn isomer)

IR (Nujol): 3300, 1770, 1660, 1615 cm$^{-1}$.

NMR (D$_2$O, δ): 1.55 (6H, s), 1.92–2.28 (2H, m), 3.13–3.44 (4H, m), 3.96–4.18 (2H, m), 4.88 and 5.22 (2H, ABq, J=15 Hz), 5.22 (1H, d, J=5 Hz), 5.82 (1H, d, J=5 Hz), 5.83 (1H, d, J=3 Hz), 7.74 (1H, d, J=3 Hz).

(9) 7β-[2-(2-Formamidothiazol-4-yl)-2-methoxyiminoacetamido]-3-(4,5,6,7-tetrahydro-1-pyrazolo[1,5-a]-pyrimidinio)methyl-3-cephem-4-carboxylate (syn isomer)

IR (Nujol): 1775, 1660, 1620 cm$^{-1}$.

NMR (DMSO-d$_6$, δ): 1.88–2.14 (2H, m), 3.18–3.37 (2H, m), 3.34 (2H, m), 3.63–4.16 (2H, m), 3.86 (3H, s), 5.18 (1H, d, J=5 Hz), 5.19 (2H, br s), 5.75 (1H, dd, J=8, 5 Hz), 5.82 (1H, d, J=3 Hz), 7.33 (1H, s), 7.99 (1H, d, J=3 Hz), 8.43 (1H, s), 9.59 (1H, d, J=8 Hz).

(10) 7β-[2-(5-Amino-1,2,4-thiadiazol-3-yl)-2-(1-carboxy-1-methylethoxyimino)acetamido]-3-(4-formyl-4,5,6,7-tetrahydro-1-pyrazolo[1,5-a]pyrimidinio)-methyl-3-cephem-4-carboxylate (syn isomer)

IR (Nujol): 1770, 1680, 1600 cm$^{-1}$.

NMR (D$_2$O+NaHCO$_3$, δ): 1.65 (6H, s), 2.18–2.62 (2H, m), 3.33 and 3.63 (2H, ABq, J=18 Hz), 3.85–4.17 (2H, m), 4.36–4.53 (2H, m), 5.24 and 5.55 (2H, ABq, J=15 Hz), 5.34 (1H, d, J=5 Hz), 5.96 (1H, d, J=5 Hz), 6.83 and 7.23 (each 1H, d, J=3 Hz), 8.24 (1H, d, J=3 Hz), 8.46 (1H, s), 8.98 (1H, s).

(11) 7β-[2-(5-Amino-1,2,4-thiadiazol-3-yl)-2-methoxyiminoacetamido]-3-(5-oxo-4,5,6,7-tetrahydro-1-pyrazolo[1,5-a]pyrimidinio)methyl-3-cephem-4-carboxylate (syn isomer)

IR (Nujol): 3300, 1765, 1700, 1660, 1590 cm$^{-1}$.

NMR (D$_2$O, δ): 3.03 (2H, t, J=8 Hz), 3.17 and 3.50 (2H, ABq, J=18 Hz), 4.07 (3H, s), 4.50 (2H, t, J=8 Hz), 5.23 (1H, d, J=5 Hz), 5.24 (2H, br s), 5.84 (1H, d, J=5 Hz), 6.17 (1H, d, J=3 Hz), 8.04 (1H, d, J=3 Hz).

(12) 7β-[2-(5-Amino-1,2,4-thiadiazol-3-yl)-2-allyloxyiminoacetamido]-3-(5-oxo-4,5,6,7-tetrahydro-1-pyrazolo-[1,5-a]pyrimidinio)methyl-3-cephem-4-carboxylate (syn isomer)

IR (Nujol): 3300, 1760, 1700, 1670, 1590 cm$^{-1}$.

NMR (D$_2$O, δ): 3.00 (2H, t, J=8 Hz), 3.16 and 3.48 (2H, ABq, J=18 Hz), 4.48 (2H, t, J=8 Hz), 4.78 (2H, d, J=6 Hz), 5.23 (1H, d, J=5 Hz), 5.21–5.44 (4H, m), 5.85 (1H, d, J=5 Hz), 6.15 (1H, d, J=3 Hz), 5.90–6.21 (1H, m), 8.02 (1H, d, J=3 Hz).

(13) 7β-[2-(5-Amino-1,2,4-thiadiazol-3-yl)-2-(1-carboxy-1-methylethoxyimino)acetamido]-3-(5-oxo-4,5,6,7-tetrahydro-1-pyrazolo[1,5-a]pyrimidinio)-methyl-3-cephem-4-carboxylate (syn isomer)

IR (Nujol): 3300, 1765, 1680, 1590 cm$^{-1}$.

NMR (D$_2$O+NaHCO$_3$, δ): 1.56 (6H, s), 3.09 (2H, t, J=8 Hz), 3.19 and 3.51 (2H, ABq, J=18 Hz), 4.56 (2H, t, J=8 Hz), 5.23 (1H, d, J=5 Hz), 5.26 (2H, br s), 5.84 (1H, d, J=5 Hz), 6.24 (1H, d, J=3 Hz), 8.08 (1H, d, J=3 Hz).

(14) 7β-[2-(5-Amino-1,2,4-thiadiazol-3-yl)-2-(1-carboxy-1-methylethoxyimino)acetamido]-3-[1-(2-hydroxyethyl)-2,3-dihydro-5-(1H-imidazo[1,2-b]pyrazolio)]methyl-3-cephem-4-carboxylate (syn isomer)

IR (Nujol): 3300, 1770, 1670, 1500 cm$^{-1}$.

NMR (D$_2$O+NaHCO$_3$, δ): 1.52 (6H, s), 3.25–3.57 (4H, m), 3.67–3.90 (2H, m), 3.97–4.47 (4H, m), 4.87–5.17 (2H, m), 5.27 (1H, d, J=5 Hz), 5.8–6.02 (2H, m), 8.01 (1H, d, J=3 Hz).

(15) 7β-[2-(5-Amino-1,2,4-thiadiazol-3-yl)-2)-allyloxyiminoacetamido]-3-[1-(2-hydroxyethyl)-2,3-dihydro-5-(1H-imidazo[1,2-b]pyrazolio)]methyl-3-cephem-4-carboxylate (syn isomer)

IR (Nujol): 3250, 1760, 1670, 1610 cm$^{-1}$.

NMR (D$_2$O, δ): 3.27–3.60 (4H, m), 3.70–3.97 (2H, m), 3.97–4.60 (4H, m), 4.77–5.60 (7H, m), 5.80–6.03 (2H, m), 5.97–6.40 (1H, m), 8.03 (1H, d, J=3Hz).

(16) 7β-[2-(2-Formamidothiazol-4-yl)-2-methoxyiminoacetamido]-3-[1-(2-hydroxyethyl)-2,3-dihydro-5-(1H-imidazo-[1,2-b]pyrazolio)]methyl-3-cephem-4-carboxylate (syn isomer)

(17) 7β-[2-(5-Amino-1,2,4-thiadiazol-3-yl)-2-(1-carboxy-1-methylethoxyimino)acetamido]-3-[7-methyl-2,3-dihydro-5-(1H-imidazo[1,2-b]pyrazolio)]methyl-3-cephem-4-carboxylate (syn isomer)

IR (Nujol): 3200–3300, 1770, 1660, 1600 cm$^{-1}$.

NMR (DMSO-d$_6$, δ): 1.54 (6H, s), 1.73 (3H, s), 3.20, 3.50 (2H, ABq, J=18 Hz, 26 Hz), 3.97–4.30 (4H, m), 4.80–5.0 (2H, m), 5.22 (1H, d, J=5 Hz), 5.82 (1H, d, J=5 Hz), 7.73 (1H, s).

(18) 7β-[2-(5-Amino-1,2,4-thiadiazol-3-yl)-2-allyloxyiminoacetamido]-3-[7-methyl-2,3-dihydro-5-(1H-imidazo-[1,2-b]pyrazolio)]methyl-3-cephem-4-carboxylate (syn isomer)

IR (Nujol): 3200–3300, 1760, 1670, 1610 cm$^{-1}$.

NMR (D$_2$O, δ): 1.93 (3H, s), 3.18, 2.47 (2H, ABq, J=18 Hz, 27 Hz), 3.90–4.40 (4H, m), 4.7–5.50 (7H, m), 5.83 (1H, d, J=5 Hz), 5.83–6.27 (1H, m), 7.71 (1H, s).

(19) 7β-[2-Formamidothiazol-4-yl)-2-methoxyiminoacetamido]-3-[7-methyl-2,3-dihydro-5-(1H-imidazo[1,2-b]pyrazolio)]methyl-3-cephem-4-carboxylate (syn isomer)

(20) 7β-[2-(5-Amino-1,2,4-thiadiazol-3-yl)-2-allyloxyiminoacetamido]-3-[1-methyl-2,3-dihydro-5-(1H-imidazo[1,2-b]pyrazolio)]methyl-3-cephem-4-carboxylate (syn isomer)

IR (Nujol): 1760, 1670, 1600 cm$^{-1}$.

NMR (D$_2$O+NaHCO$_3$, δ): 2.97 (3H, s), 3.20, 3.50 (2H, ABq, J=18 Hz, 27 Hz), 3.78-4.43 (4H, m), 4.67-5.50 (6H, m), 5.22 (1H, d, J=5 Hz), 5.85 (1H, d, J=5 Hz), 5.87 (1H, d, J=3 Hz), 5.80-6.30 (1H, m), 7.90 (1H, d, J=3 Hz).

(21) 7β-[2-Formamidothiazol-4-yl)-2-methoxyiminoacetamido]-3-[1-methyl-2,3-dihydro-5-(1H-imidazo[1,2-b]pyrazolio)]methyl-3-cephem-4-carboxylate (syn isomer)

(22) 7β-[2-(5-Amino-1,2,4-thiadiazol-3-yl)-2-(1-carboxy-1-methylethoxyimino)acetamido]-3-(6-hydroxy-4,5,6,7-tetrahydro-1-pyrazolo[1,5-a]pyrimidinio)methyl-3-cephem-4-carboxylate (syn isomer)

IR (Nujol): 3300, 1770, 1620, 1160 cm$^{-1}$.

NMR (D$_2$O, δ): 1.60 (6H, s), 3.13 (1H, d, J=18 Hz), 3.53 (1H, d, J=18 Hz), 3.23 (1H, m), 3.40 (2H, m), 4.15 (2H, m), 5.00 (2H, s), 5.13 (1H, d, J=6 Hz), 5.83 (1H, d, J=6 Hz), 5.87 (1H, d, J=3 Hz), 7.80 and 7.84 (each d, 1H, J=3 Hz).

(23) 7β-[2-(2-Aminothiazol-4-yl)-2-methoxyiminoacetamido]-3-(6-hydroxy-4,5,6,7-tetrahydro-1-pyrazolo[1,5-a]pyrimidinio)methyl-3-cephem-4-carboxylate (syn isomer)

IR (Nujol): 3300, 1770, 1620, 1040 cm$^{-1}$.

NMR (D$_2$O, δ): 3.13 (1H, d, J=18 Hz), 3.24 (1H, m), 3.42 (2H, m), 3.53 (1H, d, J=18 Hz), 4.00 (3H, s), 4.16 (2H, m), 5.01 (2H, s), 5.13 and 5.18 (1H, each d, J=6 Hz), 5.80 (1H, d, J=6 Hz), 5.87 (1H, d, J=3 Hz), 6.96 (1H, s), 7.81 and 7.83 (1H, each d, J=3 Hz).

(24) 7β-[2-(5-Amino-1,2,4-thiadiazol-3-yl)-2-methoxyiminoacetamido]-3-(6-hydroxy-4,5,6,7-tetrahydro-1-pyrazolo-[1,5-a]pyrimidinio)methyl-3-cephem-4-carboxylate (syn isomer)

IR (Nujol): 3250, 1760, 1620, 1040 cm$^{-1}$.

NMR (D$_2$O, δ): 3.13 (1H, d, J=18 Hz), 3.24 (1H, m), 3.42 (2H, m), 3.53 (1H, d, J=18 Hz), 4.06 (3H, s), 4.15 (2H, m), 5.10 (2H, s), 5.15 and 5.17 (1H, each d, J=6 Hz), 5.81 (1H, d, J=6 Hz), 5.86 (1H, d, J=3 Hz), 7.80 and 7.83 (1H, each d, J=3 Hz).

(25) 7β-[2-(5-Amino-1,2,4-thiadiazol-3-yl)-2-ethoxyiminoacetamido]-3-(4,5,6,7-tetrahydro-1-pyrazolo[1,5-a]pyrimidinio)methyl-3-cephem-4-carboxylate (syn isomer)

IR (Nujol): 1760, 1660, 1610 cm$^{-1}$.

NMR (D$_2$O, δ): 1.33 (3H, t, J=7 Hz), 1.91-2.28 (2H, m), 3.03-3.48 (4H, m), 3.92-4.18 (2H, m), 4.33 (2H, q, J=7 Hz), 4.86 and 5.23 (2H, ABq, J=16 Hz), 5.20 (1H, d, J=5 Hz), 5.79 (1H, d, J=3 Hz), 5.83 (1H, d, J=5 Hz), 7.84 (1H, d, J=3 Hz).

(26) 7β-[2-(5-Amino-1,2,4-thiadiazol-3-yl}-2-(1-carboxy-1-methylethoxyimino)acetamido]-3-[7-methylthio-2,3-dihydro-5-(1H-imidazo[1,2-b]pyrazolio)]-methyl-3-cephem-4-carboxylate (syn isomer)

IR (Nujol): 1670, 1660, 1620, 1590 cm$^{-1}$.

NMR (D$_2$O—NaHCO$_3$, δ): 1.53 (6H, s), 2.29 (3H, s), 3.21, 3.52 (2H, ABq, J=18 Hz, 26 Hz), 3.93-4.50 (4H, m), 4.88, 5.10 (2H, ABq, J=16 Hz, 20 Hz), 5.22 (1H, d, J=5 Hz), 5.82 (1H, d, J=5 Hz), 8.0 (1H, s).

(27) 7β-[2-(2-Aminothiazol-4-yl)-2-methoxyiminoacetamido]-3-[7-methylthio-2,3-dihydro-5-(1H-imidazo[1,2-b]pyrazolio)]methyl-3-cephem-4-carboxylate (syn isomer)

IR (Nujol): 1770, 1670, 1600, 1520 cm$^{-1}$.

NMR (D$_2$O—NaHCO$_3$, δ): 2.28 (3H, s), 3.20, 3.51 (2H, ABq, J=18 Hz, 26 Hz), 3.97 (3H, s), 4.03-4.47 (4H, m), 4.90, 5.05 (2H, ABq, J=10 Hz, 14 Hz), 5.20 (1H, d, J=5 Hz), 5.79 (1H, d, J=5 Hz), 6.95 (1H, s), 7.98 (1H, s).

(28) 7β-[2-(5-Amino-1,2,4-thiadiazol-3-yl)-2-ethoxyiminoacetamido]-3-[7-methylthio-2,3-dihydro-5-(1H-imidazo-[1,2-b]pyrazolio)]methyl-3-cephem-4-carboxylate (syn isomer)

IR (Nujol): 1770, 1660, 1600, 1525 cm$^{-1}$.

NMR (D$_2$O—NaHCO$_3$, δ): 1.33 (3H, t, J=7 Hz), 2.30 (3H, s), 3.22, 3.52 (2H, ABq, J=18 Hz, 26 Hz), 3.92-4.53 (6H, m), 4.87-5.12 (2H, m), 5.23 (1H, d, J=5 Hz), 5.84 (1H, d, J=5 Hz), 8.0 (1H, s).

(29) 7β-[2-(5-Amino-1,2,4-thiadiazol-3-yl)-2-ethoxyiminoacetamido]-3-[2,3-dihydro-5-(1H-imidazo[1,2-b]pyrazolio)]methyl-3-cephem-4-carboxylate (syn isomer)

IR (Nujol): 1770, 1670, 1520 cm$^{-1}$.

NMR (D$_2$O—NaHCO$_3$, δ): 1.34 (3H, t, J=7 Hz), 3.22, 3.52 (2H, ABq, J=18 Hz, 26 Hz), 3.90-4.50 (4H, m), 4.90, 5.16 (2H, ABq, J=16 Hz, 24 Hz), 5.23 (1H, d, J=5 Hz), 5.82 (1H, d, J=3 Hz), 5.84 (1H, d, J=5 Hz), 7.90 (1H, d, J=3 Hz).

(30) 7β-[2-(2-Aminothiazol-4-yl)-2-allyloxyiminoacetamido]-3-[2,3-dihydro-5-(1H-imidazo[1,2-b]pyrazolio)]-methyl-3-cephem-4-carboxylate (syn isomer)

IR (Nujol): 1770, 1660, 1600, 1520 cm$^{-1}$.

NMR (D$_2$O—NaHCO$_3$, δ): 3.21, 3.51 (2H, ABq, J=18 Hz, 26 Hz), 3.90-4.53 (4H, m), 4.92, 5.14 (2H, ABq, J=16 Hz, 20 Hz), 5.23 (1H, d, J=5 Hz), 4.92-5.56 (4H, m), 5.82 (1H, d, J=5 Hz), 5.83 (1H, d, J=2 Hz), 5.70-6.30 (1H, m), 6.97 (1H, s), 7.89 (1H, d, J=2 Hz).

(31) 7β-[2-(2-Aminothiazol-4-yl)-2-ethoxyiminoacetamido]-3-[2,3-dihydro-5-(1H-imidazo[1,2-b]pyrazolio)]methyl-3-cephem-4-carboxylate (syn isomer)

NMR (D$_2$O, δ): 1.31 (3H, t, J=7 Hz), 3.21, 3.50 (2H, ABq, J=18 Hz, 26 Hz), 3.90-4.47 (4H, m), 4.89, 5.13 (2H, ABq, J=16 Hz, 22 Hz), 5.22 (1H, d, J=5 Hz), 5.81 (1H, d, J=3 Hz), 6.93 (1H, s), 7.88 (1H, d, J=3 Hz).

(32) 7β-[2-(5-Amino-1,2,4-thiadiazol-3-yl)-2-carboxymethoxyiminoacetamido]-3-(4,5,6,7-tetrahydro-1-pyrazolo-[1,5-a]pyrimidinio)methyl-3-cephem-4-carboxylate (syn isomer)

IR (Nujol): 1770, 1670, 1620, 1520 cm$^{-1}$.

NMR (D$_2$O, δ): 1.92-2.33 (2H, m), 3.14 and 3.42 (2H, ABq, J=15 Hz), 3.05-3.53 (2H, m), 3.85-4.23 (2H, m), 4.65 (2H, br s), 4.96 and 5.20 (2H, ABq, J=18 Hz), 5.16 (1H, d, J=5 Hz), 5.80 (1H, d, J=3 Hz), 5.83 (1H, d, J=5 Hz), 7.75 (1H, d, J=3 Hz).

(33) 7β-[2-(2-Aminothiazol-4-yl)-2-ethoxyiminoacetamido]-3-(4,5,6,7-tetrahydro-1-pyrazolo[1,5-a]pyrimidinio)methyl-3-cephem-4-carboxylate (syn isomer)

IR (Nujol): 1770, 1650, 1615, 1525 cm$^{-1}$.

NMR (D$_2$O, δ): 1.32 (3H, t, J=7 Hz), 1.93-2.33 (2H, m), 3.06-3.53 (4H, m), 3.90-4.18 (2H, m), 4.25 (2H, q, J=7 Hz), 4.86 and 5.20 (2H, ABq, J=18 Hz), 5.21 (1H, d, J=5 Hz), 5.80 (1H, d, J=3 Hz), 5.84 (1H, d, J=5 Hz), 6.94 (1H, s), 7.75 (1H, d, J=3 Hz).

(34) 7β-[2-(2-Aminothiazol-4-yl)-2-allyloxyiminoacetamido]-3-(4,5,6,7-tetrahydro-1-pyrazolo[1,5-a]pyrimidinio)methyl-3-cephem-4-carboxylate (syn isomer)

IR (Nujol): 1765, 1650, 1610, 1520 cm$^{-1}$.

NMR (D$_2$O, δ): 1.93-2.35 (2H, m), 3.13 and 3.43 (2H, ABq, J=15 Hz), 3.10-3.53 (2H, m), 3.93-4.23 (2H, m), 4.70 (2H, br s), 4.86 and 5.56 (2H, ABq, J=18 Hz), 5.08-5.50 (2H, m), 5.23 (1H, d, J=5 Hz), 5.84 (1H, d, J=3 Hz), 5.86 (1H, d, J=5 Hz), 5.85-6.30 (1H, m), 6.98 (1H, s), 7.75 (1H, d, J=3 Hz).

(35) 7β-[2-(2-Aminothiazol-4-yl)-2-methoxyiminoacetamido]- 3-[2,3-dihydro-5-(1H-imidazo[1,2-b]pyrazolio)]methyl-3-cephem-4-carboxylate (syn isomer)

IR (Nujol): 1770, 1660, 1600, 1530 cm$^{-1}$.

(36) 7β-[2-(2-Aminothiazol-4-yl)-2-methoxyiminoacetamido]-3-(4-methyl-4,5,6,7-tetrahydro-1-pyrazolo[1,5-a]pyrimidinio)methyl-3-cephem-4-carboxylate (syn isomer)

IR (Nujol): 3200, 1760, 1660, 1610 cm$^{-1}$.

(37) 7β-[2-(2-Aminothiazol-4-yl)-2-methoxyiminoacetamido]-3-(4,5,6,7-tetrahydro-1-pyrazolo[1,5-a]pyrimidinio)methyl-3-cephem-4-carboxylate (syn isomer)

IR (Nujol): 3250, 1760, 1660, 1610 cm$^{-1}$.

(38) 7β-[2-(2-Aminothiazol-4-yl)-2-methoxyiminoacetamido]-3-[1-(2-hydroxyethyl)-2,3-dihydro-5-(1H-imidazo-[1,2-b]pyrazolio)methyl-3-cephem-4-carboxylate (syn isomer)

IR (Nujol): 3250, 1760, 1660, 1610 cm$^{-1}$.

(39) 7β-[2-(2-Aminothiazol-4-yl)-2-methoxyiminoacetamido]-3-[7-methyl-2,3-dihydro-5-(1H-imidazo[1,2-b]pyrazolio)]methyl-3-cephem-4-carboxylate (syn isomer)

IR (Nujol): 3200-3300, 1760, 1660, 1610 cm$^{-1}$.

(40) 7β-[2-(2-Aminothiazol-4-yl)-2-methoxyiminoacetamido]-3-[1-methyl-2,3-dihydro-5-(1H-imidazo[1,2-b]pyrazolio)]methyl-3-cephem-4-carboxylate (syn isomer)

IR (Nujol): 1770, 1670, 1610 cm$^{-1}$.

EXAMPLE 6

To a suspension of 7β-[2-(2-formamidothiazol-4-yl)-2-methoxyiminoacetamido]-3-[2,3-dihydro-5-(1H-imidazo-[1,2-b]pyrazolio)]methyl-3-cephem-4-carboxylate (syn isomer) (3.4 g) in methanol (17 ml) was added concentrated hydrochloric acid (0.74 ml) at room temperature. The mixture was stirred at ambient temperature for 2 hours. The reaction mixture was poured into ethyl acetate (170 ml). The resultant powder was collected by filtration, dissolved in water and adjusted to pH 2.5 with a saturated aqueous solution of sodium bicarbonate. The solution was subjected to column chromatography on "Diaion HP-20" using 5% aqueous isopropyl alcohol as an eluent. Fractions containing the object compound were combined and evaporated to remove isopropyl alcohol. The residue was lyophilized to give 7β-[2-(2-aminothiazol-4-yl)-2-methoxyiminoacetamido]-3-[2,3-dihydro-5-(1H-imidazo-[1,2-b]pyrazolio)]methyl-3-cephem-4-carboxylate (syn isomer) (0.35 g).

IR (Nujol): 1770, 1660, 1600, 1530 cm$^{-1}$.

NMR (D$_2$O, δ): 3.21 (1H, d, J=18 Hz), 3.51 (1H, d, J=18 Hz), 3.98 (3H, s), 3.97-4.47 (4H, m), 4.89 (1H, d, J=13 Hz), 5.12 (1H, d, J=13 Hz), 5.21 (1H, d, J=5 Hz), 5.79 (1H, d, J=5 Hz), 5.82 (1H, d, J=3 Hz), 6.96 (1H, s), 7.89 (1H, d, J=3 Hz).

EXAMPLE 7

The following compounds were obtained according to a similar manner to that of Example 6.

(1) 7β-[2-[2-Aminothiazol-4-yl)-2-methoxyiminoacetamido]-3-(4-methyl-4,5,6,7-tetrahydro-1-pyrazolo[1,5-a]-pyrimidinio)methyl-3-cephem-4-carboxylate (syn isomer)

IR (Nujol): 3200, 1760, 1660, 1610 cm$^{-1}$.

NMR (D$_2$O, δ): 1.97-2.32 (2H, m), 3.00 (3H, s), 3.11-3.43 (4H, m), 3.83-4.13 (2H, m), 3.97 (3H, s), 4.87 and 5.21 (2H, ABq, J=16 Hz), 5.18 (1H, d, J=5 Hz), 5.79 (1H, d, J=5 Hz), 5.88 (1H, d, J=3 Hz), 6.93 (1H, s), 7.76 (1H, d, J=3 Hz).

(2) 7β-[2-(2-Aminothiazol-4-yl)-2-methoxyiminoacetamido]-3-(4,5,6,7-tetrahydro-1-pyrazolo[1,5-a]pyrimidinio)methyl-3-cephem-4-carboxylate (syn isomer)

IR (Nujol): 3250, 1760, 1660, 1610 cm$^{-1}$.

NMR (D$_2$O, δ): 1.92-2.28 (2H, m), 3.13-3.49 (4H, m), 3.88-4.24 (2H, m), 3.97 (3H, m), 4.85 and 5.20 (2H, ABq, J=15 Hz), 5.17 (1H, d, J=5 Hz), 5.77 (1H, d, J=5 Hz), 5.78 (1H, d, J=3 Hz), 6.95 (1H, s), 7.72 (1H, d, J=3 Hz).

(3) 7β-[2-(2-Aminothiazol-4-yl)-2-methoxyiminoacetamido]-3-[1-(2-hydroxyethyl)-2,3-dihydro-5-(1H-imidazo[1,2-b]-pyrazolio)]methyl-3-cephem-4-carboxylate (syn isomer)

IR (Nujol): 3250, 1760, 1660, 1610 cm$^{-1}$.

NMR (D$_2$O, δ): 3.30-3.62 (4H, m), 3.73-3.97 (2H, m), 4.07 (3H, s), 4.10-4.43 (4H, m), 4.93, 5.20 (2H, ABq, J=18 Hz, 24 Hz), 5.30 (1H, d, J=5 Hz), 5.90 (1H, d, J=5 Hz), 5.95 (1H, d, J=5 Hz), 7.07 (1H, s), 8.03 (1H, d, J=3 Hz).

(4) 7β-[2-(2-Aminothiazol-4-yl)-2-methoxyiminoacetamido]-3-[1-methyl-2,3-dihydro-5-(1H-imidazo[1,2-b]pyrazolio)]methyl-3-cephem-4-carboxylate (syn isomer)

IR (Nujol): 3200-3300, 1760, 1660, 1610 cm$^{-1}$.

NMR (DMSO-d$_6$, δ): 1.90 (3H, s), 3.10-3.67 (2H, m), 3.83 (3H, s), 3.90-4.60 (4H, m), 4.80-5.17 (3H, m), 5.57 (1H, d, J=5 Hz, 8 Hz), 6.69 (1H, s), 7.16 (2H, br s), 8.03 (1H, s), 9.44 (1H, d, J=8 Hz).

(5) 7β-[2-(2-Aminothiazol-4-yl)-2-methoxyiminoacetamido]-3-[1-methyl-2,3-dihydro-5-(1H-imidazo[1,2-b]pyrazolio)]methyl-3-cephem-4-carboxylate (syn isomer)

IR (Nujol): 1770, 1670, 1610 cm$^{-1}$.

NMR (D$_2$O, δ): 2.96 (3H, s), 3.20, 3.49 (2H, ABq, J=18 Hz, 26 Hz), 3.97 (3H, s), 3.77-4.37 (4H, m), 4.83, 5.05 (2H, ABq, J=15 Hz, 21 Hz), 5.19 (1H, d, J=5 Hz), 5.77 (1H, d, J=5 Hz), 5.82 (1H, d, J=3 Hz), 6.94 (1H, s), 7.88 (1H, d, J=3 Hz).

EXAMPLE 8

7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate (syn isomer) (1 g) was dissolved in a mixture of 1N hydrochloric acid (1.64 ml) and water (100 ml) at ambient temperature. The solution was lyophilized to give 7β-[2-(5-amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate hydrochloride (syn isomer) (1.04 g)

IR (Nujol): 3270, 1780, 1720, 1675, 1600 cm$^{-1}$.

NMR (D$_2$O, δ): 1.61 (6H, s), 3.29 and 3.60 (2H, ABq, J=18 Hz), 3.97-4.44 (4H, m), 5.12 (2H, br s), 5.28 (1H, d, J=5 Hz), 5.85 (1H, d, J=3 Hz), 5.88 (1H, d, J=5 Hz), 7.93 (1H, d, J=3 Hz).

EXAMPLE 9

To a solution of 7β-[2-(5-amino-1,2,4-thiadiazol-3-yl)-2-allyloxyiminoacetamido]-3-(4,5,6,7-tetrahydro-1-pyrazolo[1,5-a]pyrimidinio)methyl-3-cephem-4-carboxylate (syn isomer) (1 g) in water (3 ml) was added 2N hydrochloric acid (1 ml) at room temperature. The mixture was stirred at ambient temperature for 3 hours, and the resulting precipitate was collected by filtration to give 7β-[2-(5-amino-1,2,4-thiadiazol-3-yl)-2-allyloxyiminoacetamido]-3-(4,5,6,7-tetrahydro-1-pyrazolo[1,5-a]-pyrimidinio)methyl-3-cephem-4-carboxylate hydrochloride (syn isomer) (202 mg) as crystals.

IR (Nujol): 3400, 3240, 1790, 1710, 1640, 1620, 1600 cm$^{-1}$.

NMR (DMSO-d$_6$, δ): 1.81-2.28 (2H, m), 3.05-3.52 (4H, m), 3.71-4.32 (2H, m), 4.63 (2H, d, J=6 Hz), 5.00-5.41 (4H, m), 5.17 (1H, d, J=5 Hz), 5.78 (1H, d, J=8, 5 Hz), 5.83-6.18 (1H, m), 5.85 (1H, d, J=3 Hz), 8.04 (1H, d, J=3 Hz), 8.17 (2H, br s), 8.25 (1H, br s), 9.56 (1H, d, J=8 Hz).

EXAMPLE 10

7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate (syn isomer) (1 g) was dissolved in a mixture of 1M sulfuric acid (1.64 ml) and water 100 ml) at ambient temperature. The solution was lyophilized to give 7β--[2-(5-amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer) (1.19 g).

IR (Nujol): 3250, 1780, 1670, 1600 cm$^{-1}$.

NMR (D$_2$O, δ): 1.60 (6H, s), 3.26 and 3.60 (2H, ABq, J=18 Hz), 3.95-4.46 (4H, m), 5.10 (2H, br s), 5.26 (1H, d, J=5 Hz), 5.85 (1H, d, J=5 Hz), 5.90 (1H, d, J=3 Hz), 5.93 (1H, d, J=3 Hz).

EXAMPLE 11

To a mixture of 2M sulfuric acid (1.52 ml) and ethanol (1.52 ml) was added 7β-[2-(2-aminothiazol-4-yl)-2-methoxyiminoacetamido]-3-(4,5,6,7-tetrahydro-1-pyrazolo-[1,5-a]pyrimidinio)methyl-3-cephem-4-carboxylate (syn isomer) (0.76 g) at room temperature. The mixture was stirred at ambient temperature for 4 hours, and the resulting precipitate was collected by filtration to give 7β-[2-(2-aminothiazol-4-yl)-2-methoxyiminoacetamido]-3-(4,5,6,7-tetrahydro-1-pyrazolo[1,5-a]pyrimidinio)methyl-3-cephem-4-carboxylate sulfate (syn isomer) (462 mg) as crystals.

IR (Nujol): 3600, 3425, 3180, 1795, 1675, 1640, 1610 cm$^{-1}$.

NMR (DMSO-d$_6$, δ): 1.81-2.23 (2H, m), 3.12-3.43 (4H, m), 3.83 (3H, s), 3.87-4.26 (2H, m), 4.96-5.36 (2H, m), 5.16 (1H, d, J=5 Hz), 5.78 (1H, dd, J=8, 5 Hz), 5.86 (1H, d, J=3 Hz), 6.72 (1H, s), 7.96 (1H, d, J=3 Hz), 9.55 (1H, d, J=8 Hz).

EXAMPLE 12

To a suspension of 7β-(2-(5-amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate (syn isomer)(0.5 g) in acetonitrile (1 ml) was added 2M sulfuric acid (0.5 ml) at ambient temperature. The mixture was stirred for 30 minutes. The resulting precipitate was collected by filtration to give 7β-[2-(5-amino-1,2,4-thiadiazol-3-yl)-2-(1-carboxy-1-methylethoxyimino)acetamido]-3-(4,5,6,7-tetrahydro-1-pyrazolo[1,5-a]-pyrimidinio)methyl-3-cephem-4-carboxylate sulfate (syn isomer) as crystals (380 mg).

IR (Nujol): 3250, 1780, 1750, 1665, 1635, 1610 cm$^{-1}$.

NMR (D$_2$O, δ): 1.60 (6H, s), 1.93-2.32 (2H, m), 3.10-3.57 (4H, m), 3.92-4.18 (2H, m), 5.15 (2H, br s), 5.24 (1H, d, J=5 Hz), 5.82 (1H, d, J=3 Hz), 5.86 (1H, d, J=5 Hz), 7.74 (1H, d, J=3 Hz).

EXAMPLE 13

The following compounds were obtained according to similar manners to those of Examples 10-12.

(1) 7β-[2-(2-Aminothiazol-4-yl)-2-allyloxyiminoacetamido]-3-[2,3-dihydro-5-(1H-imidazo[1,2-b]pyrazolio)]methyl-3-cephem-4-carboxylate sulfate (syn isomer) (crystal)

IR (Nujol): 3570, 1780, 1640, 1595, 1535 cm$^{-1}$.

NMR (D$_2$O—NaHCO$_3$, δ): 3.27, 3.55 (2H, ABq, J=18 Hz, 26 Hz), 3.98-4.50 (4H, m), 4.94, 5.17 (2H, ABq, J=16 Hz, 20 Hz), 4.97-5.57 (4H, m), 5.22 (1H, d, J=5 Hz), 5.83 (1H, d, J=5 Hz), 5.88 (1H, d, J=3 Hz), 5.77-6.32 (1H, m), 7.07 (1H, s), 7.93 (1H, d, J=3 Hz).

(2) 7β-[2-(2-Aminothiazol-4-yl)-2-ethoxyiminoacetamido]-3-[2,3-dihydro-5-(1H-imidazo[1,2-b]pyrazolio)]methyl-3-cephem-4-carboxylate sulfate (syn isomer) (crystal)

IR (Nujol): 3220, 1780, 1660, 1600, 1580 cm$^{-1}$.

NMR (D$_2$O—NaHCO$_3$, δ): 1.33 (3H, t, J=7 Hz), 3.25, 3.53 (2H, ABq, J=18 Hz, 26 Hz), 3.93-4.47 (4H, m), 4.91, 5.15 (2H, ABq, J=16 Hz, 22 Hz), 5.23 (1H, d, J=5 Hz), 5.81 (1H, d, J=5 Hz), 5,85 (1H, d, J=3 Hz), 7.03 (1H, s), 7.92 (1H, d, J=3 Hz).

(3) 7β-[2-(2-Aminothiazol-4-yl)-2-ethoxyiminoacetamido]-3-(4,5,6,7-tetrahydro-1-pyrazolo[1,5-a]pyrimidinio)methyl-3-cephem-4-carboxylate sulfate (syn isomer) (crystal)

IR (Nujol): 3220, 1785, 1655, 1630, 1560 cm$^{-1}$.

NMR (DMSO-d$_6$, δ): 1.25 (3H, t, J=7 Hz), 1.80-2.25 (2H, m), 3.05-3.50 (4H, m), 3.80-4.30 (4H, m), 5.18 (1H, d, J=5 Hz), 5.80 (1H, d, J=3 Hz), 5.82 (1H, dd, J=5 Hz, 8 Hz), 6.72 (1H, s), 9.55 (1H, d, J=8 Hz).

(4) 7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-carboxylate sulfate (syn isomer) (crystal)

IR (Nujol): 3200, 1780, 1735, 1650, 1540 cm$^{-1}$.

NMR (D$_2$O—NaHCO$_3$, δ): 1.55 (6H, s), 3.20 and 3.50 (2H, ABq, J=18 Hz), 3.97-4.44 (2H, m), 4.92 and 5.10 (2H, ABq, J=16 Hz), 5.23 (1H, d, J=5 Hz), 5.82 (1H, d, J=3 Hz), 5.83 (1H, d, J=5 Hz), 7.89 (1H, d, J=3 Hz).

EXAMPLE 14

To a solution of 7β-amino-3-[1-(2-formamidoethyl)-2,3-dihydro-5-(1H-imidazo[1,2-b]pyrazolio)]methyl-3-cephem-4-carboxylate bis(trifluoroacetate) (1.17 g), N-(trimethylsilyl)acetamide (2.5 g) and tetrahydrofuran (25 ml) was added 2-(5-amino-1,2,4-thiadiazol-3-yl)-2-(1-t-butoxycarbonyl-1-methylethoxyimino)acetic methanesulfonic anhydride (syn isomer) (0.85 g) under ice-cooling. The mixture was stirred at room temperature for 2 hours. The reaction mixture was poured into a mixture of ethyl acetate (25 ml) and diisopropyl ether (25 ml). The resultant powder was collected by filtration. To the powder in methanol (10 ml) was added conc. hydrochloric acid (0.67 ml). The mixture was stirred for hours at room temperature. The reaction mixture was poured into ethyl acetate (100 ml). The resultant powder was collected by filtration. To a solution of the powder in a mixture of methylene chloride (3 ml) and anisole (1 ml) was added dropwise trifluoroacetic acid (2 ml) under ice-cooling. The mixture was stirred for 2 hours at room temperature. The reaction mixture was poured into a mixture of diisopropyl ether (30 ml) and ethyl acetate (30 ml). The resultant powder was collected by filtration, dissolved in water and adjusted to pH 3 with a saturated aqueous solution of sodium bicarbonate. The solution was subjected to column chromatography on HP-20 using 10% aqueous isopropyl alcohol as an eluent. Fractions containing the object compound were combined, evaporated to remove isopropyl alcohol and lyophilized to give 7μ-[2-(5-amino-1,2,4-thiadiazol-3-yl)-2-(1-carboxy-1-methylethoxyimino)acetamido]-3-[1-(2-aminoethyl)-2,3-dihydro-5-(1H-imidazo[1,2-b]pyrazolio)]-methyl-3-cephem-4-carboxylate (syn isomer) (0.23 g).

IR (Nujol): 1775, 1590, 1520 cm$^{-1}$.

NMR (D$_2$O—NaHCO$_3$, δ): 1.55 (9H, s), 3.20, 3.54 (2H, ABq, J=18 Hz, 24 Hz), 3.13-3.73 (4H, m), 3.95-4.33 (4H, m), 4.80-5.12 (2H, m), 5.23 (1H, d, J=5 Hz), 5.82 (1H, d, J=5 Hz), 5.94 (1H, d, J=3 Hz), 7.95 (1H, d, J=3 Hz).

EXAMPLE 15

To a suspension of 7β-[2-(2-aminothiazol-4-yl)-2-t-butoxycarbonylmethoxyiminoacetamido]-3-(4,5,6,7-tetrahydro-1-pyrazolo[1,5-a]pyrimidinio)methyl-3-cephem-4-carboxylate (syn isomer) (800 mg) in methylene chloride (2.4 ml) and anisole (0.8 ml) was added dropwise trifluoroacetic acid (1.6 ml) at 20° C. The stirring was continued for 3 hours at the room temperature. The reaction mixture was poured into ethyl acetate. The resulting precipitates were collected by filtration. The precipitates were dissolved in water (50 ml) and the mixture was adjusted to pH 6.5 with a saturated aqueous solution of sodium bicarbonate. The solution was subjected to column chromatography on HP-20 using water as an eluent and the object fractions were adjusted to pH 2.0 with 1N hydrochloric acid. The resulting solution was subjected to column chromatography on HP-20 using 15% aqueous isopropyl alcohol as an eluent and the object fractions were lyophilized to give 7β-[2-(2-aminothiazol-4-yl)-2-carboxymethoxyiminoacetamido]-3-(4,5,6,7-tetrahydro-1-pyrazolo[1,5-a]pyrimidinio)methyl-3-cephem-4-carboxylate (syn isomer) (300 mg).

IR (Nujol): 1765, 1660, 1610, 1520 cm$^{-1}$.

NMR (D$_2$O—NaHCO$_3$, δ): 1.93-2.28 (2H, m), 3.13 and 3.40 (2H, ABq, J=15 Hz), 3.05-3.50 (2H, m), 3.83-4.18 (2H, m), 4.55 (2H, br s), 4.88 and 5.12 (2H, ABq, J=18 Hz), 5.16 (1H, d, J=5 Hz), 5.80 (1H, d, J=3 Hz), 5.83 (1H, d, J=5 Hz), 6.95 (1H, s), 7.70 (1H, d, J=3 Hz).

EXAMPLE 16

The following compounds were obtained according to similar manners to those of Examples 1-4.

(1) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate hydrochloride (syn isomer)

IR (Nujol): 3270, 1780, 1720, 1675, 1600 cm$^{-1}$.

(2) 7β-[2-(5-Amino-1,2,4-thiadiazol-3-yl)-2-allyloxyiminoacetamido]-3-(4,5,6,7-tetrahydro-1-pyrazolo[1,5-a]pyrimidinio)methyl-3-cephem-4-carboxylate hydrochloride (syn isomer)

IR (Nujol): 3400, 3240, 1790, 1710, 1640, 1620, 1600 cm$^{-1}$.

(3) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer)

IR (Nujol): 3250, 1780, 1670, 1600 cm$^{-1}$.

(4) 7β-[2-(2-Aminothiazol-4-yl)-2-methoxyiminoacetamido]-3-(4,5,6,7-tetrahydro-1-pyrazolo[1,5-a]pyrimidinio)methyl-3-cephem-4-carboxylate sulfate (syn isomer)

IR (Nujol): 3600, 3425, 3180, 1795, 1675, 1640, 1610 cm$^{-1}$.

(5) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate sulfate (syn isomer)

IR (Nujol): 3250, 1780, 1750, 1665, 1635, 1610 cm$^{-1}$.

(6) 7β-[2-(2-Aminothiazol-4-yl)-2-allyloxyiminoacetamido]-3-[2,3-dihydro-5-(1H-imidazo[1,2-b]pyrazolio)]methyl-3-cephem-4-carboxylate sulfate (syn isomer)

IR (Nujol): 3570, 1780, 1640, 1595, 1535 cm$^{-1}$.

(7) 7β-[2-(2-Aminothiazol-4-yl)-2-ethoxyiminoacetamido]-3-[2,3-dihydro-5-(1H-imidazo[1,2-b]pyrazolio)]methyl-3-cephem-4-carboxylate sulfate (syn isomer)

IR (Nujol): 3220, 1780, 1660, 1600, 1580 cm$^{-1}$.

(8) 7β-[2-(2-Aminothiazol-4-yl)-2-ethoxyiminoacetamido]-3-(4,5,6,7-tetrahydro-1-pyrazolo[1,5-a]pyrimidinio)methyl-3-cephem-4-carboxylate sulfate (syn isomer)

IR (Nujol): 3220, 1785, 1655, 1630, 1560 cm$^{-1}$.

(9) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer)

IR (Nujol): 3200, 1780, 1735, 1650, 1540 cm$^{-1}$.

(10) 7β-[2-(2-Aminothiazol-4-yl)-2-t-butoxycarbonylmethoxyiminoacetamido]-3-(4,5,6,7-tetrahydro-1-pyrazolo[1,5-a]pyrimidinio)methyl-3-cephem-4-carboxylate (syn isomer)

NMR (D$_2$O—NaHCO$_3$, δ): 1.53 (9H, s), 1.98-2.23 (2H, m), 3.08-3.50 (4H, m), 3.85-4.20 (2H, m), 4.61 (2H, br s), 4.18-5.13 (2H, m), 5.21 (1H, d, J=5 Hz), 5.78 (1H, d, J=3 Hz), 5.81 (1H, d, J=5 Hz), 6.88 (1H, s), 7.73 (1H, d, J=3 Hz).

(11) 7β-[2-(2-Aminothiazol-4-yl)-2-(1-t-butoxycarbonyl-1-methylethoxyimino)acetamido]-3-(4,5,6,7-tetrahydro-1-pyrazolo[1,5-a]pyrimidinio)methyl-3-cephem-4-carboxylate (syn isomer)

NMR (D$_2$O—NaHCO$_3$, δ): 1.45 (6H, s), 1.53 (9H, s), 1.95-2.30 (2H, m), 3.00-3.53 (4H, m), 3.88-4.23 (2H, m), 4.90-5.20 (2H, m), 5.21 (1H, d, J=5 Hz), 5.78 (1H, d, J=3 Hz), 5.85 (1H, d, J=5 Hz), 6.94 (1H, s), 7.72 (1H, d, J=3 Hz).

(12) 7β-[2-(5-Amino-1,2,4-thiadiazol-3-yl)-2-(1-carboxy-1-methylethoxyimino)acetamido]-3-[1-(2-aminoethyl)-2,3-dihydro-5-(1H-imidazo[1,2-b]pyrazolio)]methyl-3-cephem-4-carboxylate (syn isomer)

IR (Nujol): 1775, 1590, 1520 cm$^{-1}$.

(13) 7β-[2-(2-Aminothiazol-4-yl)-2-carboxymethoxyiminoacetamido]-3-(4,5,6,7-tetrahydro-1-pyrazolo[1,5-a]pyrimidinio)methyl-3-cephem-4-carboxylate(syn isomer)

(14) 7β-[2-(2-Aminothiazol-4-yl]-2-(1-carboxy-1-methylethoxyimino)acetamido]-3-(4,5,6,7-tetrahydro-1-pyrazolo-[1,5-a]pyrimidinio)methyl-3-cephem-4-carboxylate (syn isomer)
IR (Nujol): 1770, 1660, 1620, 1525 cm$^{-1}$.

EXAMPLE 17

The following compounds were obtained according to a similar manner to that of Example 6.
(1) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate (syn isomer)
IR (Nujol): 3300, 1770, 1670, 1600, 1520 cm$^{-1}$.
(2) 7β-[2-(5-Amino-1,2,4-thiadiazol-3-yl)-2-(1-carboxy-1-methylethoxyimino)acetamido]-3-[1-methyl-2,3-dihydro-5-(1H-imidazo[1,2-b]pyrazolio)]methyl-3-cephem-4-carboxylate (syn isomer)
IR (Nujol) 3250, 1770, 1670 cm$^{-1}$.
(3) 7β-[2-(2-Aminothiazol-4-yl)-2-methoxyiminoacetamido]-3-(5-oxo-4,5,6,7-tetrahydro-1-pyrazolo[1,5-a]pyrimidinio)methyl-3-cephem-4-carboxylate (syn isomer)
IR (Nujol): 3300, 1765, 1700, 1660 cm$^{-1}$.
(4) 7β-[2-(5-Amino-1,2,4-thiadiazol-3-yl)-2-methoxyiminoacetamido]-3-[2,3-dihydro-5-(1H-imidazo[1,2-b]pyrazolio)]methyl-3-cephem-4-carboxylate (syn isomer)
IR (Nujol): 3250, 1670, 1600, 1520 cm$^{-1}$.
(5) 7β-[2-(5-Amino-1,2,4-thiadiazol-3-yl)-2-allyloxyiminoacetamido]-3-[2,3-dihydro-5-(1H-imidazo[1,2-b]pyrazolio)]methyl-3-cephem-4-carboxylate (syn isomer)
IR (Nujol): 3300, 1770, 1670, 1600, 1520 cm$^{-1}$.
(6) 7β-[2-(5-Amino-1,2,4-thiadiazol-3-yl)-2-(1-carboxy-1-methylethoxyimino)acetamido]-3-(4-methyl-4,5,6,7-tetrahydro-1-pyrazolo[1,5-a]pyrimidinio)-methyl-3-cephem-4-carboxylate (syn isomer)
IR (Nujol): 3250, 1760, 1660, 1620 cm$^{-1}$.
(7) 7β-[2-(5-Amino-1,2,4-thiadiazol-3-yl)-2-allyloxyiminoacetamido]-3-(4-methyl-4,5,6,7-tetrahydro-1-pyrazolo[1,5-a]pyrimidinio)methyl-3-cephem-4-carboxylate (syn isomer)
IR (Nujol): 3300, 1760, 1670, 1615 cm$^{-1}$.
(8) 7β-[2-(5-Amino-1,2,4-thiadiazol-3-yl)-2-methoxyiminoacetamido]-3-(4,5,6,7-tetrahydro-1-pyrazolo[1,5-a]pyrimidinio)methyl-3-cephem-4-carboxylate (syn isomer)
IR (Nujol): 3200, 1760, 1650, 1605 cm$^{-1}$.
(9) 7β-[2-(5-Amino-1,2,4-thiadiazol-3-yl)-2-allyloxyiminoacetamido]-3-(4,5,6,7-tetrahydro-1-pyrazolo[1,5-a]pyrimidinio)methyl-3-cephem-4-carboxylate (syn isomer)
IR (Nujol): 3250, 1760, 1660, 1600 cm$^{-1}$.
(10) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate (syn isomer)
IR (Nujol): 3300, 1770, 1660, 1615 cm$^{-1}$.
(11) 7β-[2-(5-Amino-1,2,4-thiadiazol-3-yl}-2-(1-carboxy-1-methylethoxyimino)acetamido]-3-(4-formyl-4,5,6,7-tetrahydro-1-pyrazolo[1,5-a]pyrimidinio)-methyl-3-cephem-4-carboxylate (syn isomer)
IR (Nujol): 1770, 1680, 1600 cm$^{-1}$.
(12) 7β-[2-(5-Amino-1,2,4-thiadiazol-3-yl)-2-methoxyiminoacetamido]-3-(5-oxo-4,5,6,7-tetrahydro-1-pyrazolo[1,5-a]pyrimidinio)methyl-3-cephem-4-carboxylate (syn isomer)
IR (Nujol): 3300, 1765, 1700, 1660, 1590 cm$^{-1}$.
(13) 7β-[2-(5-Amino-1,2,4-thiadiazol-3-yl)-2-allyloxyiminoacetamido]-3-(5-oxo-4,5,6,7-tetrahydro-1-pyrazolo-[1,5-a]pyrimidinio)methyl-3-cephem-4-carboxylate (syn isomer)
IR (Nujol): 3300, 1760, 1700, 1670, 1590 cm$^{-1}$.
(14) 7β-[2-(5-Amino-1,2,4-thiadiazol-3-yl)-2-(1-carboxy-1-methylethoxyimino)acetamido]-3-(5-oxo-4,5,6,7-tetrahydro-1-pyrazolo[1,5-a]pyrimidinio)-methyl-3-cephem-4-carboxylate (syn isomer)
IR (Nujol): 3300, 1765, 1680, 1590 cm$^{-1}$.
(15) 7β-[2-(5-Amino-1,2,4-thiadiazol-3-yl)-2-(1-carboxy-1-methylethoxyimino)acetamido]-3-[1-(2-hydroxyethyl)-2,3-dihydro-5-(1H-imidazo[1,2-b]pyrazolio)]methyl-3-cephem-4-carboxylate (syn isomer)
IR (Nujol): 3300, 1770, 1670, 1500 cm$^{-1}$.
(16) 7β-[2-(5-Amino-1,2,4-thiadiazol-3-yl)-2-allyloxyiminoacetamido]-3-[1-(2-hydroxyethyl)-2,3-dihydro-5-(1H-imidazo[1,2-b]pyrazolio)]methyl-3-cephem-4-carboxylate (syn isomer)
IR (Nujol): 3250, 1760, 1670, 1610 cm$^{-1}$.
(17) 7β-[2-(5-Amino-1,2,4-thiadiazol-3-yl)-2-(1-carboxy-1-methylethoxyimino)acetamido]-3-[7-methyl-2,3-dihydro-5-(1H-imidazo[1,2-b]pyrazolio)]methyl-3-cephem-4-carboxylate (syn isomer)
IR (Nujol): 3200-3300, 1770, 1660, 1600 cm$^{-1}$.
(18) 7β-[2-(5-Amino-1,2,4-thiadiazol-3-yl)-2-allyloxyiminoacetamido]-3-[7-methyl-2,3-dihydro-5-(1H-imidazo-[1,2-b]pyrazolio)]methyl-3-cephem-4-carboxylate (syn isomer)
IR (Nujol): 3200-3300, 1760, 1670, 1610 cm$^{-1}$.
(19) 7β-[2-(5-Amino-1,2,4-thiadiazol-3-yl)-2-allyloxyiminoacetamido]-3-[1-methyl-2,3-dihydro-5-(1H-imidazo-[1,2-b]pyrazolio)]methyl-3-cephem-4-carboxylate (syn isomer)
IR (Nujol): 1760, 1670, 1600 cm$^{-1}$.
(20) 7β-[2-(5-Amino-1,2,4-thiadiazol-3-yl)-2-(1-carboxy-1-methylethoxyimino)acetamido]-3-(6-hydroxy-4,5,6,7-tetrahydro-1-pyrazolo[1,5-a]pyrimidinio)methyl-3-cephem-4-carboxylate (syn isomer)
IR (Nujol) 3300, 1770, 1620, 1160 cm$^{-1}$.
(21) 7β-[2-(2-Aminothiazol-4-yl)-2-methoxyiminoacetamido]-3-(6-hydroxy-4,5,6,7-tetrahydro-1-pyrazolo[1,5-a]pyrimidinio)methyl-3-cephem-4-carboxylate (syn isomer)
IR (Nujol): 3300, 1770, 1620, 1040 cm$^{-1}$.
(22) 7β-[2-(5-Amino-1,2,4-thiadiazol-3-yl)-2-methoxyiminoacetamido]-3-(6-hydroxy-4,5,6,7-tetrahydro-1-pyrazolo-[1,5-a]pyrimidinio)methyl-3-cephem-4-carboxylate (syn isomer)
IR (Nujol): 3250, 1760, 1620, 1040 cm$^{-1}$.
(23) 7β-[2-(5-Amino-1,2,4-thiadiazol-3-yl)-2-ethoxyiminoacetamido]-3-(4,5,6,7-tetrahydro-1-pyrazolo[1,5-a]pyrimidinio)methyl-3-cephem-4-carboxylate (syn isomer)
IR (Nujol): 1760, 1660, 1610 cm$^{-1}$.
(24) 7β-[2-(5-Amino-1,2,4-thiadiazol-3-yl)-2-(1-carboxy-1-methylethoxyimino)acetamido]-3-[7-methylthio-2,3-dihydro-5-(1H-imidazo[1,2-b]pyrazolio)]-methyl-3-cephem-4-carboxylate (syn isomer)
IR (Nujol): 1670, 1660, 1620, 1590 cm$^{-1}$.
(25) 7β-[2-(2-Aminothiazol-4-yl)-2-methoxyiminoacetamido]-3-[7-methylthio-2,3-dihydro-5-

(1H-imidazo[1,2-b]pyrazolio)]methyl-3-cephem-4-carboxylate (syn isomer)
IR (Nujol): 1770, 1670, 1600, 1520 cm$^{-1}$.

(26) 7β-[2-(5-Amino-1,2,4-thiadiazol-3-yl)-2-ethoxyiminoacetamido]-3-[7-methylthio-2,3-dihydro-5-(1H-imidazo-[1,2-b]pyrazolio)]methyl-3-cephem-4-carboxylate (syn isomer)
IR (Nujol): 1770, 1660, 1600, 1525 cm$^{-1}$.

(27) 7β-[2-(5-Amino-1,2,4-thiadiazol-3-yl)-2-ethoxyiminoacetamido]-3-[2,3-dihydro-5-(1H-imidazo[1,2-b]pyrazolio)]methyl- 3-cephem-4-carboxylate (syn isomer)
IR (Nujol): 1770, 1670, 1520 cm$^{-1}$.

(28) 7β-[2-(2-Aminothiazol-4-yl)-2-allyloxyiminoacetamido]-3-[2,3-dihydro-5-(1H-imidazo[1,2-b]pyrazolio)]methyl-3-cephem-4-carboxylate (syn isomer)
IR (Nujol): 1770, 1660, 1600, 1520 cm$^{-1}$.

(29) 7β-[2-(2-Aminothiazol-4-yl)-2-ethoxyiminoacetamido]-3-[2,3-dihydro-5-(1H-imidazo[1,2-b]pyrazolio)]methyl-3-cephem-4-carboxylate (syn isomer)
NMR (D$_2$O, δ): 1.31 (3H, t, J=7 Hz), 3.21, 3.50 (2H, ABq, J=18 Hz, 26 Hz), 3.90-4.47 (4H, m), 4.89, 5.13 (2H, ABq, J=16 Hz, 22 Hz), 5.22 (1H, d, J=5 Hz), 5.81 (1H, d, J=3 Hz), 6.93 (1H, s), 7.88 (1H, d, J=3 Hz).

(30) 7β-[2-(5-Amino-1,2,4-thiadiazol-3-yl)-2-carboxymethoxyiminoacetamido]-3-(4,5,6,7-tetrahydro-1-pyrazolo-[1,5-a]pyrimidinio)methyl-3-cephem-4-carboxylate (syn isomer)
IR (Nujol): 1770, 1670, 1620, 1520 cm$^{-1}$.

(31) 7β-[2-(2-Aminothiazol-4-yl)-2-ethoxyiminoacetamido]-3-(4,5,6,7-tetrahydro-1-pyrazolo[1,5-a]pyrimidinio)methyl-3-cephem-4-carboxylate (syn isomer)
IR (Nujol): 1770, 1650, 1615, 1525 cm$^{-1}$.

(32) 7β-[2-(2-Aminothiazol-4-yl)-2-allyloxyiminoacetamido]-3-(4,5,6,7-tetrahydro-1-pyrazolo[1,5-a]-pyrimidinio)methyl-3-cephem-4-carboxylate (syn isomer)
IR (Nujol): 1765, 1650, 1610, 1520 cm$^{-1}$.

(33) 7β-[2-(5-Amino-1,2,4-thiadiazol-3-yl)-2-(1-carboxy-1-methylethoxyimino)acetamido]-3-[2,3-dihydro-5-(1H-imidazo[ 1,2-b]pyrazolio)]methyl-3-cephem-4-carboxylate hydrochloride (syn isomer)
IR (Nujol): 3270, 1780, 1720, 1675, 1600 cm$^{-1}$.

(34) 7β-[2-(5-Amino-1,2,4-thiadiazol-3-yl)-2-allyloxyiminoacetamido]-3-(4,5,6,7-tetrahydro-1-pyrazolo[1,5-a]pyrimidinio)methyl-3-cephem-4-carboxylate hydrochloride (syn isomer)
IR (Nujol): 3400, 3240, 1790, 1710, 1640, 1620, 1600 cm$^{-1}$.

(35) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer)
IR (Nujol): 3250, 1780, 1670, 1600 cm$^{-1}$.

(36) 7β-[2-(2-Aminothiazol-4-yl)-2-methoxyiminoacetamido]-3-(4,5,6,7-tetrahydro-1-pyrazolo[1,5-a]pyrimidinio)methyl-3-cephem-4-carboxylate sulfate (syn isomer)
IR (Nujol): 3600, 3425, 3180, 1795, 1675, 1640, 1610 cm$^{-1}$.

(37) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate sulfate (syn isomer)
IR (Nujol): 3250, 1780, 1750, 1665, 1635, 1610 cm$^{-1}$.

(38) 7β-[2-(2-Aminothiazol-4-yl)-2-allyloxyiminoacetamido]-3-[2,3-dihydro-5-(1H-imidazo[1,2-b]pyrazolio)]methyl-3-cephem-4-carboxylate sulfate (syn isomer)
IR (Nujol): 3570, 1780, 1640, 1595, 1535 cm$^{-1}$.

(39) 7β-[2-(2-Aminothiazol-4-yl)-2-ethoxyiminoacetamido]- 3-[2,3-dihydro-5-(1H-imidazo[1,2-b]pyrazolio)]methyl-3-cephem-4-carboxylate sulfate (syn isomer)
IR (Nujol): 3220, 1780, 1660, 1600, 1580 cm$^{-1}$.

(40) 7β-[2-(2-Aminothiazol-4-yl)-2-ethoxyiminoacetamido]-3-(4,5,6,7-tetrahydro-1-pyrazolo[1,5-a]pyrimidinio)methyl-3-cephem-4-carboxylate sulfate (syn isomer)
IR (Nujol): 3220, 1785, 1655, 1630, 1560 cm$^{-1}$.

(41) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer)
IR (Nujol): 3200, 1780, 1735, 1650, 1540 cm$^{-1}$.

(42) 7β-[2-(2-Aminothiazol-4-yl)-2-t-butoxycarbonylmethoxyiminoacetamido]-3-(4,5,6,7-tetrahydro-1-pyrazolo-[1,5-a]pyrimidinio)methyl-3-cephem-4-carboxylate (syn isomer)
NMR (D$_2$O—NaHCO$_3$, δ): 1.53 (9H, s), 1.98-2.23 (2H, m), 3.08-3.50 (4H, m), 3.85-4.20 (2H, m), 4.61 (2H, br s), 4.18-5.13 (2H, m), 5.21 (1H, d, J=5 Hz), 5.78 (1H, d, J=3 Hz), 5.81 (1H, d, J=5 Hz), 6.88 (1H, s), 7.73 (1H, d, J=3 Hz).

(43) 7β-[2-(2-Aminothiazol-4-yl)-2-(1-t-butoxycarbonyl-1-methylethoxyimino)acetamido]-3-(4,5,6,7-tetrahydro-1-pyrazolo[1,5-a]pyrimidinio)methyl-3-cephem-4-carboxylate (syn isomer)
NMR (D$_2$O—NaHCO$_3$, δ): 1.45 (6H, s), 1.53 (9H, s), 1.95-2.30 (2H, m), 3.00-3.53 (4H, m), 3.88-4.23 (2H, m), 4.90-5.20 (2H, m), 5.21 (1H, d, J=5 Hz), 5.78 (1H, d, J=3 Hz), 5.85 (1H, d, J=5 Hz), 6.94 (1H, s), 7.72 (1H, d, J=3 Hz).

(44) 7β-[2-(5-Amino-1,2,4-thiadiazol-3-yl)-2-(1-carboxy-1-methylethoxyimino)acetamido]-3-[1-(2-aminoethyl)-2,3-dihydro-5-(1H-imidazo[1,2-b]pyrazolio)]methyl-3-cephem-4-carboxylate (syn isomer)
IR (Nujol): 1775, 1590, 1520 cm$^{-1}$.

(45) 7β-[2-(2-Aminothiazol-4-yl)-2-carboxymethoxyiminoacetamido]-3-(4,5,6,7-tetrahydro-1-pyrazolo[1,5-a]pyrimidinio)methyl-3-cephem-4-carboxylate (syn isomer)
IR (Nujol) 1765, 1660, 1610, 1520 cm$^{-1}$.

(46) 7β-[2-(2-Aminothiazol-4-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate (syn isomer)
IR (Nujol): 1770, 1660, 1620, 1525 cm$^{-1}$.

EXAMPLE 18

The following compounds were obtained according to a similar manner to that of Example 15.

(1) 7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate (syn isomer)
IR (Nujol): 3300, 1770, 1670, 1600, 1520 cm$^{-1}$.

(2) 7β-[2-(5-Amino-1,2,4-thiadiazol-3-yl)-2-(1-carboxy-1-methylethoxyimino)acetamido]-3-[1-methyl-2,3-dihydro-5-(1H-imidazo[1,2-b]pyrazolio)]methyl-3-cephem-4-carboxylate (syn isomer)
IR (Nujol): 3250, 1770, 1670 cm$^{-1}$.

(3) 7β-[2-(5-Amino-1,2,4-thiadiazol-3-yl)-2-(1-carboxy-1-methylethoxyimino)acetamido]-3-(4-methyl-4,5,6,7-tetrahydro-1-pyrazolo[1,5-a]pyrimidinio)-methyl-3-cephem-4-carboxylate (syn isomer)
IR (Nujol): 3250, 1760, 1660, 1620 cm$^{-1}$.

(4) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate (syn isomer)
IR (Nujol): 3300, 1770, 1660, 1615 cm$^{-1}$.

(5) 7β-[2-(5-Amino-1,2,4-thiadiazol-3-yl)-2-(1-carboxy-1-methylethoxyimino)acetamido]-3-(4-formyl-4,5,6,7-tetrahydro-1-pyrazolo[1,5-a]pyrimidinio)-methyl-3-cephem-4-carboxylate (syn isomer)
IR (Nujol): 1770, 1680, 1600 cm$^{-1}$.

(6) 7β-[2-(5-Amino-1,2,4-thiadiazol-3-yl)-2-(1-carboxy-1-methylethoxyimino)acetamido]-3-(5-oxo-4,5,6,7-tetrahydro-1-pyrazolo[1,5-a]pyrimidinio)methyl-3-cephem-4-carboxylate (syn isomer)
IR (Nujol): 3300, 1765, 1680, 1590 cm$^{-1}$.

(7) 7β-[2-(5-Amino-1,2,4-thiadiazol-3-yl)-2-(1-carboxy-1-methylethoxyimino)acetamido]-3-[1-(2-hydroxyethyl)-2,3-dihydro-5-(1H-imidazo[1,2-b]pyrazolio)]-methyl-3-cephem-4-carboxylate (syn isomer)
IR (Nujol): 3300, 1770, 1670, 1500 cm$^{-1}$.

(8) 7β-[2-(5-Amino-1,2,4-thiadiazol-3-yl)-2-(1-carboxy-1-methylethoxyimino)acetamido]-3-[7-methyl-2,3-dihydro-5-(1H-imidazo[1,2-b]pyrazolio)]methyl-3-cephem-4-carboxylate (syn isomer)
IR (Nujol): 3200-3300, 1770, 1660, 1600 cm$^{-1}$.

(9) 7β-[2-(5-Amino-1,2,4-thiadiazol-3-yl)-2-(1-carboxy-1-methylethoxyimino)acetamido]- 3-(6-hydroxy-4,5,6,7-tetrahydro-1-pyrazolo[1,5-a]pyrimidinio)-methyl-3-cephem-4-carboxylate (syn isomer)
IR (Nujol): 3300, 1770, 1620, 1160 cm$^{-1}$.

(10) 7β-[2-(5-Amino-1,2,4-thiadiazol-3-yl)-2-(1-carboxy-1-methylethoxyimino)acetamido]-3-[7-methylthio-2,3-dihydro-5-(1H-imidazo[1,2-b]pyrazolio)]-methyl-3-cephem-4-carboxylate (syn isomer)
IR (Nujol): 1670, 1660, 1620, 1590 cm$^{-1}$.

(11) 7β-[2-(5-Amino-1,2,4-thiadiazol-3-yl)-2-carboxymethoxyiminoacetamido]-3-(4,5,6,7-tetrahydro-1-pyrazolo-[1,5-a]pyrimidinio)methyl-3-cephem-4-carboxylate (syn isomer)
IR (Nujol): 1770, 1670, 1620, 1520 cm$^{-1}$.

(12) 7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate hydrochloride (syn isomer)
IR (Nujol): 3270, 1780, 1720, 1675, 1600 cm$^{-1}$.

(13) 7β-[2-(5-Amino-1,2,4-thiadiazol-3-yl)-2-(1-carboxy-1-methylethoxyimino)acetamido]-3-[2,3-dihydro-5-(1H-imidazo[1,2-b]pyrazolio)]methyl-3-cephem-4-carboxylate sulfate (syn isomer)
IR (Nujol): 3250, 1780, 1670, 1600 cm$^{-1}$.

(14) 7β-[2-(5-Amino-1,2,4-thiadiazol-3-yl)-2-(1-carboxy-1-methylethoxyimino)acetamido]-3-(4,5,6,7-tetrahydro-1-pyrazolo[1,5-a]pyrimidinio)methyl-3-cephem-4-carboxylate sulfate (syn isomer)
IR (Nujol): 3250, 1780, 1750, 1665, 1635, 1610 cm$^{-1}$.

(15) 7β-[2-(5-Amino-1,2,4-thiadiazol-3-yl)-2-(1-carboxy-1-methylethoxyimino)acetamido]-3-[2,3-dihydro-5-(1H-imidazo-[1,2-b]pyrazolio)]methyl-3-cephem-4-carboxylate sulfate (syn isomer)
IR (Nujol): 3200, 1780, 1735, 1650, 1540 cm$^{-1}$.

(16) 7β-[2-(5-Amino-1,2,4-thiadiazol-3-yl)-2-(1-carboxy-1-methylethoxyimino)acetamido]-3-[1-(2-aminoethyl)-2,3-dihydro-5-(1H-imidazo[1,2-b]pyrazolio)]methyl-3-cephem-4-carboxylate (syn isomer)
IR (Nujol): 1775, 1590, 1520 cm$^{-1}$.

(17) 7β-[2-(2-Aminothiazol-4-yl)-2-(1-carboxy-1-methylethoxyimino)acetamido]-3-(4,5,6,7-tetrahydro-1-pyrazolo-[1,5-a]pyrimidinio)methyl-3-cephem-4-carboxylate (syn isomer)
IR (Nujol): 1770, 1660, 1620, 1525 cm$^{-1}$.
NMR (D$_2$O—NaHCO$_3$, δ): 1.52 (6H, s), 1.90-2.28 (2H, m), 3.13 and 3.40 (2H, ABq, J=18 Hz), 3.13-3.45 (2H, m), 3.80-4.18 (2H, m), 4.90 and 5.23 (2H, ABq, J=18 Hz), 5.17 (1H, d, J=5 Hz), 5.81 (1H, d, J=3 Hz), 5.84 (1H, d, J=5 Hz), 6.93 (1H, s), 7.73 1H, d, J=3 Hz).

What we claim is:

1. A compound of the formula:

wherein
R$^1$ is amino or a protected amino group,
R$^2$ is lower alkyl, lower alkenyl, carboxy (lower)alkyl or protected carboxy(lower)alkyl,
R$^3$ is hydrogen, lower alkyl, hydroxy(lower)alkyl, protected hydroxy(lower)alkyl, amino(lower)alkyl, protected amino(lower)alkyl or lower alkanoyl,
R$^4$ is hydrogen, lower alkyl or lower alkylthio, and
Z is N or CH,
and a pharmaceutically acceptable salt thereof.

2. The compound of claim 1, wherein
R$^3$ and R$^4$ are each hydrogen.

3. The compound of claim 2, wherein
R$^2$ is lower alkyl, lower alkenyl, carboxy(lower)alkyl or lower alkoxycarbonyl(lower)alkyl.

4. The compound of claim 3, wherein
R$^2$ is lower alkyl, lower alkenyl or carboxy(lower)alkyl.

5. The compound of claim 4, wherein
R$^1$ is amino, and
R$^2$ is lower alkyl.

6. The compound of claim 5, wherein
Z is CH.

7. The compound of claim 6, which is 7β-[2-(2-aminothiazol-4-yl)-2-methoxyiminoacetamido]-3-[2,3-dihydro-5-(1H-imidazo[1,2-b]pyrazolio]methyl-3-cephem-4-carboxylate (syn isomer).

8. The compound of claim 5, wherein
Z is N.

9. The compound of claim 8, which is 7β-[2-(5-amino-1,2,4-thiadiazol-3-yl)-2-methoxyiminoacetamido]-3-[2,3-dihydro-5-(1H-imidazo[1,2-b]pyrazolio)]methyl-3-cephem-4-carboxylate (syn isomer).

10. The compound of claim 8, which is 7β-[2-(5-amino-1,2,4-thiadiazol-3-yl)-2-ethoxyiminoacetamido]-3-[2,3-dihydro-5-(1H-imidazo[1,2-b]pyrazolio)]methyl-3-cephem-4-carboxylate (syn isomer).

11. An antibacterial pharmaceutical composition which comprises, as an active ingredient, an effective amount of a compound of claim 1 or a pharmaceutically acceptable salt thereof in admixture with pharmaceutically acceptable carriers.

12. A method for the treatment of infectious diseases caused by pathogenic bacteria which comprises administering an effective amount of a compound of claim 1 or a pharmaceutically acceptable salt thereof to a human or animal.

* * * * *